(12) United States Patent
Zumeris et al.

(10) Patent No.: US 6,964,640 B2
(45) Date of Patent: Nov. 15, 2005

(54) SYSTEM AND METHOD FOR DETECTION OF MOTION

(75) Inventors: Jona Zumeris, Nesher (IL); Jacob Levy, Haifa (IL); Yanina Zumeris, Nesher (IL)

(73) Assignee: P M G Medica L I D, Nesher (IL)

( * ) Notice: Subject to any disclaimer, the term of this patent is extended or adjusted under 35 U.S.C. 154(b) by 0 days.

(21) Appl. No.: 10/348,351

(22) Filed: Jan. 22, 2003

(65) Prior Publication Data

US 2003/0153831 A1 Aug. 14, 2003

Related U.S. Application Data

(60) Provisional application No. 60/349,385, filed on Jan. 22, 2002.

(51) Int. Cl.$^7$ ............................................... A61B 8/00
(52) U.S. Cl. ..................................................... 600/459
(58) Field of Search ............................ 600/443, 459–462, 600/437, 438, 447, 454–456, 561, 587; 310/330–334, 336; 73/602, 625

(56) References Cited

U.S. PATENT DOCUMENTS

| | | |
|---|---|---|
| 4,141,347 A | 2/1979 | Green et al. |
| 4,182,173 A | 1/1980 | Papadofrangakis et al. |
| 4,201,105 A | 5/1980 | Alles |
| 4,250,894 A * | 2/1981 | Frei et al. .................... 600/587 |
| 4,313,444 A * | 2/1982 | Glenn ......................... 600/441 |
| 4,336,808 A * | 6/1982 | Ohno et al. .................. 600/459 |
| 4,413,629 A | 11/1983 | Durley, III |
| 4,416,286 A | 11/1983 | Iinuma et al. |
| 4,534,357 A | 8/1985 | Powers |
| 4,542,746 A | 9/1985 | Takamizawa |
| 4,966,152 A | 10/1990 | Gang et al. |
| 5,035,245 A | 7/1991 | Nakamura et al. |
| 5,099,848 A * | 3/1992 | Parker et al. ................ 600/443 |
| 5,161,535 A | 11/1992 | Short et al. |
| 5,315,999 A | 5/1994 | Kinicki et al. |
| 5,360,005 A | 11/1994 | Wilk |
| 5,379,771 A | 1/1995 | Kawasaki et al. |
| 5,590,648 A | 1/1997 | Mitchell et al. |
| 5,606,971 A * | 3/1997 | Sarvazyan ................... 600/438 |

(Continued)

OTHER PUBLICATIONS

Pulse Oximetery—Theory IEEE Biomedical Engineering Handbook pp. 1349–1352.
BioMedical Technology—Reflectance Pulse Oximetry Groningen—Division of Artificial Organs University of Groningen.
OxiFirst Fetal Oxygen Saturation Monitoring System—Clinical Use Guide Mallinckrodt.

*Primary Examiner*—Francis J. Jaworski
(74) *Attorney, Agent, or Firm*—Pearl Cohen Zedek Laizer LLP

(57) ABSTRACT

As part of the present invention, a motion detector for detecting motion inside of a body may include a first oscillator to produce an electrical scanning signal and a second oscillator to produce an electrical Doppler signal. A vibrating element may vibrate in response to the scanning and Doppler signals. A vibration transducer may receive vibrations reflected from a structure inside the body and may convert the reflected vibrations into an electrical signal. Doppler shifts between the transmitted and received vibrations may be used to estimate the velocity of the structure inside the body.

25 Claims, 23 Drawing Sheets

U.S. PATENT DOCUMENTS

| | | |
|---|---|---|
| 5,634,459 A | 6/1997 | Gardosi |
| 5,642,171 A | 6/1997 | Baumgartner et al. |
| 5,659,466 A | 8/1997 | Norris et al. |
| 5,666,959 A | 9/1997 | Deans et al. |
| 5,671,736 A | 9/1997 | Pettit et al. |
| 5,680,865 A | 10/1997 | Tanaka |
| 5,795,297 A | 8/1998 | Daigle |
| 5,810,731 A * | 9/1998 | Sarvazyan et al. .......... 600/438 |
| 5,817,035 A | 10/1998 | Sullivan |
| 5,844,140 A * | 12/1998 | Seale ......................... 73/633 |
| 5,865,733 A | 2/1999 | Malinouskas et al. |
| 5,879,293 A | 3/1999 | Hojaiban et al. |
| 5,882,300 A | 3/1999 | Malinouskas et al. |
| 5,954,663 A | 9/1999 | Gat |
| 5,957,855 A | 9/1999 | Oriol et al. |
| 5,974,383 A | 10/1999 | Fado et al. |
| 6,045,500 A | 4/2000 | Bieniarz |
| 6,063,030 A | 5/2000 | Vara et al. |
| 6,068,597 A * | 5/2000 | Lin ............................ 600/443 |
| 6,088,609 A | 7/2000 | Larison, II |
| 6,093,151 A | 7/2000 | Shine et al. |
| 6,178,343 B1 | 1/2001 | Bindszus et al. |
| 6,231,524 B1 | 5/2001 | Wallace et al. |
| 6,245,025 B1 | 6/2001 | Török et al. |
| 6,289,206 B1 | 9/2001 | Chiang |
| 6,289,238 B1 | 9/2001 | Besson et al. |
| 6,350,237 B1 | 2/2002 | Pelletier et al. |
| 6,454,716 B1 | 9/2002 | Zumeris |
| 6,740,033 B1 | 5/2004 | Olejniczak et al. |
| 2001/0051766 A1 | 12/2001 | Gazdzinski |
| 2003/0153831 A1 | 8/2003 | Zumeris et al. |

* cited by examiner

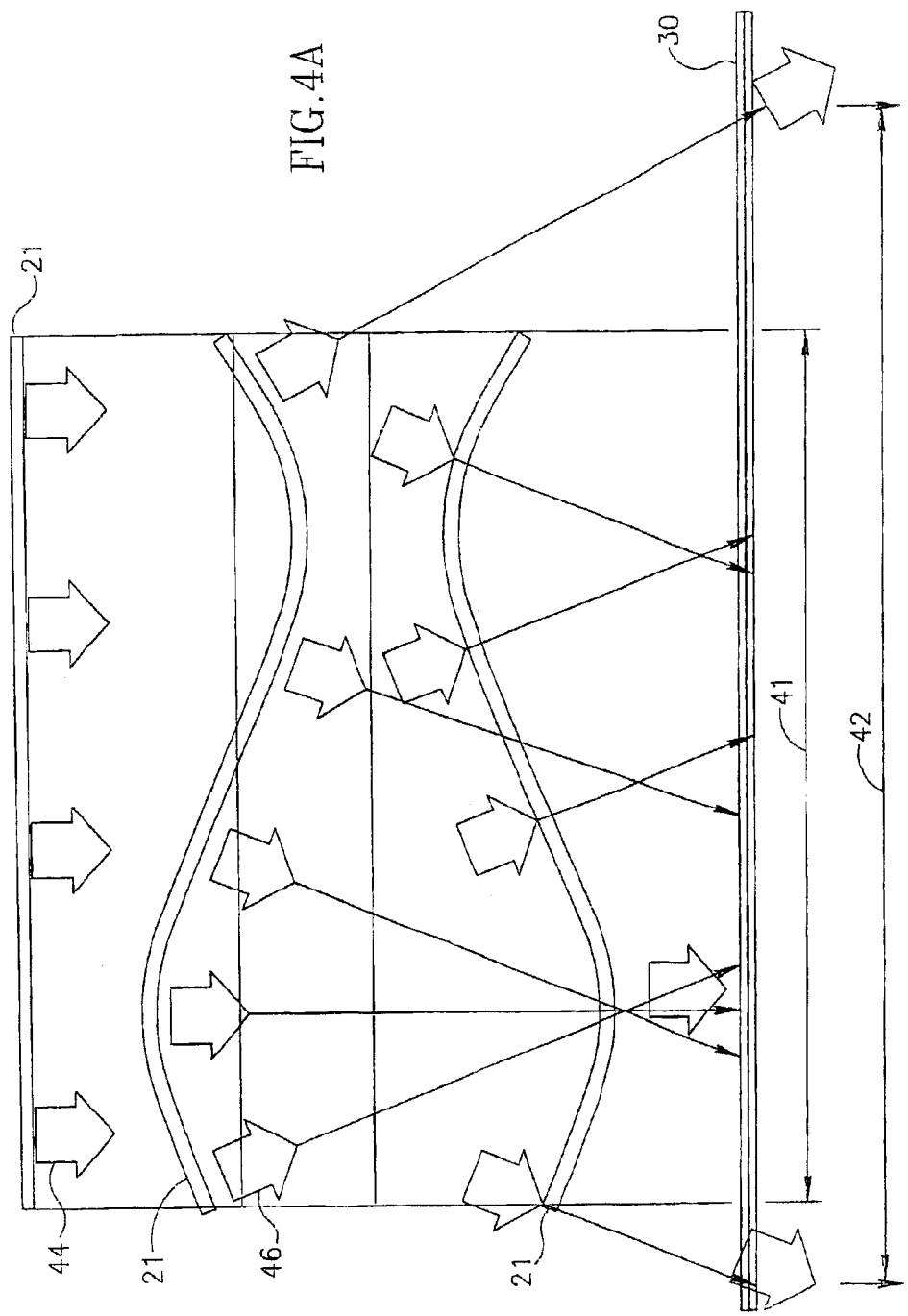

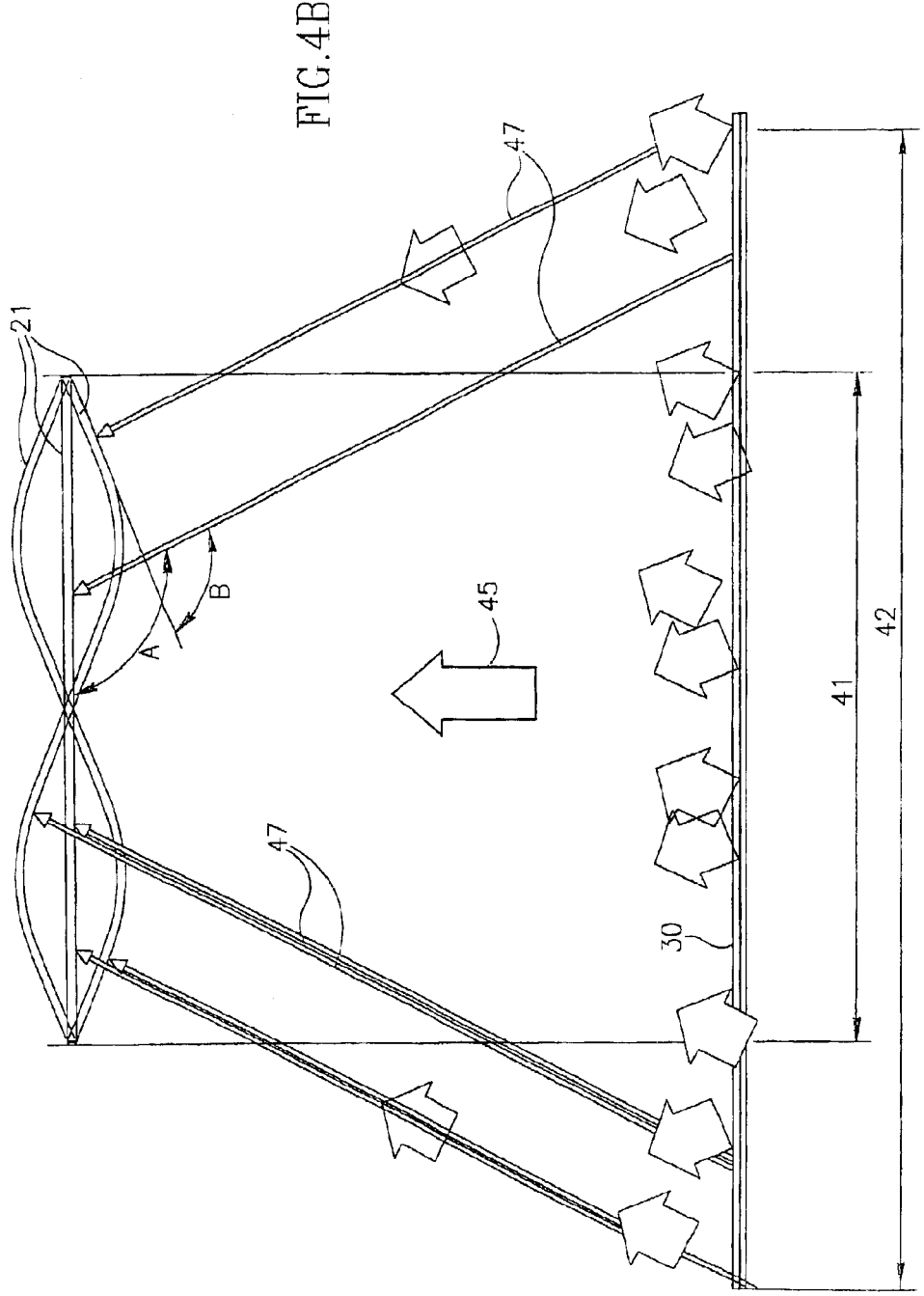

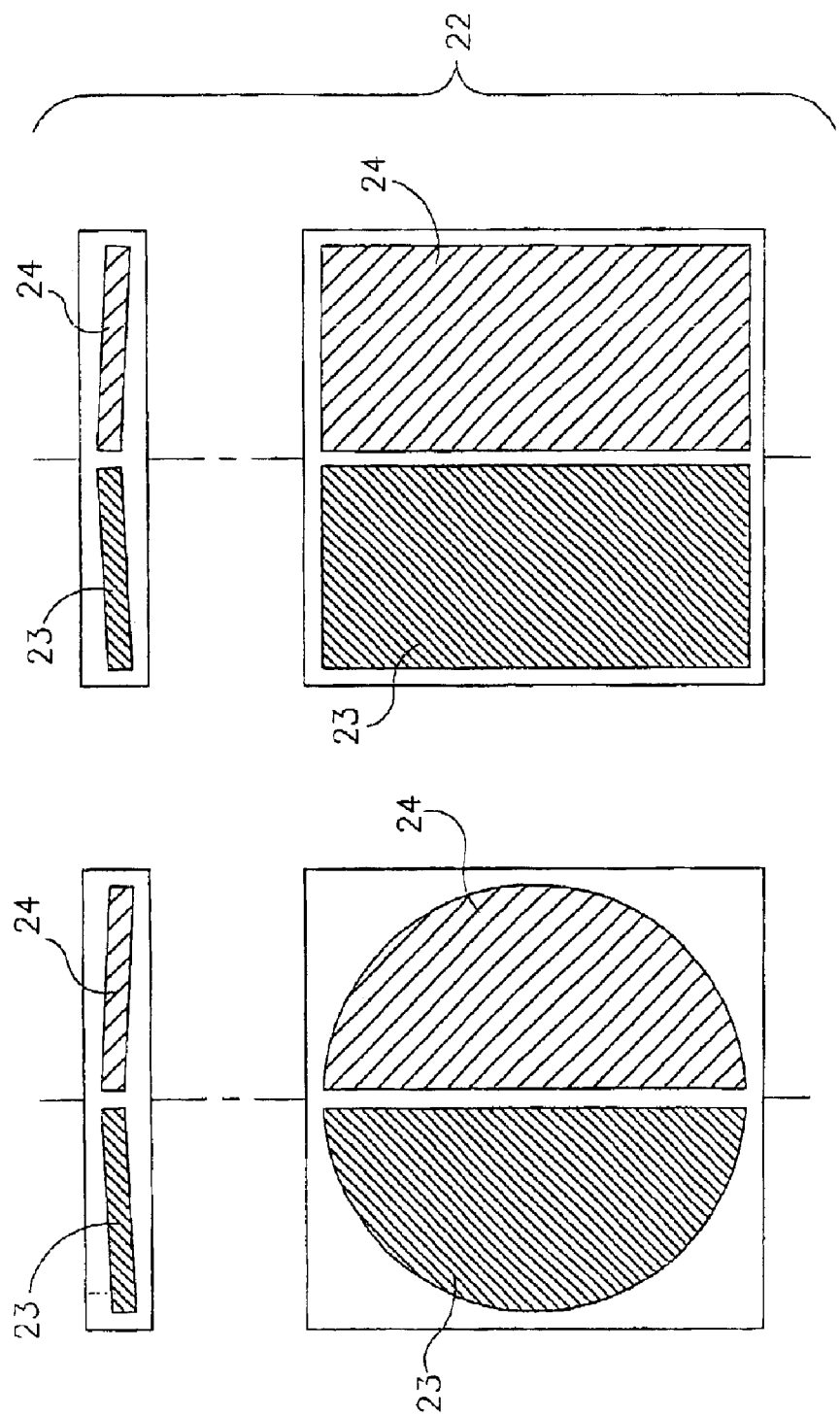

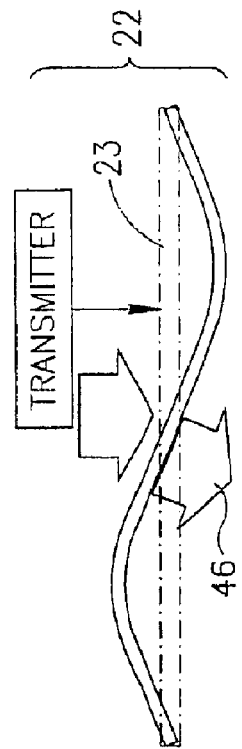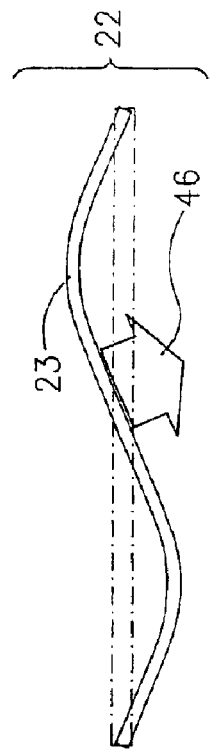
FIG.11A
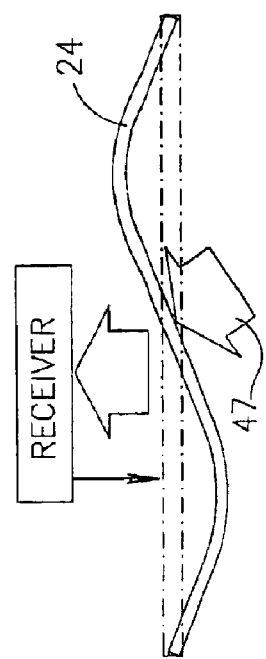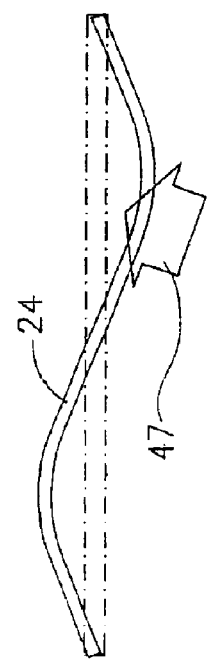
FIG.11B

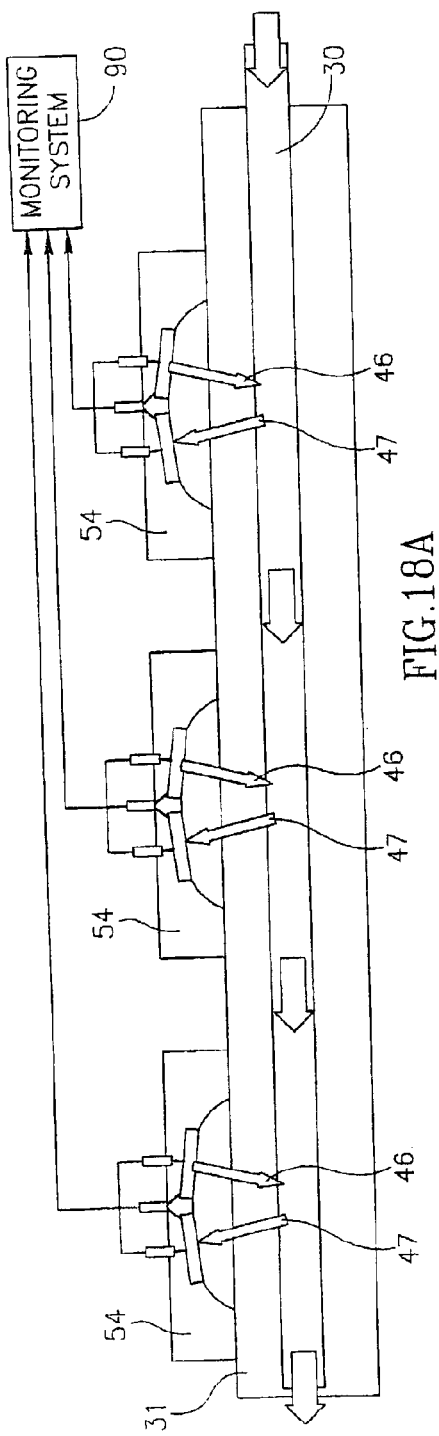
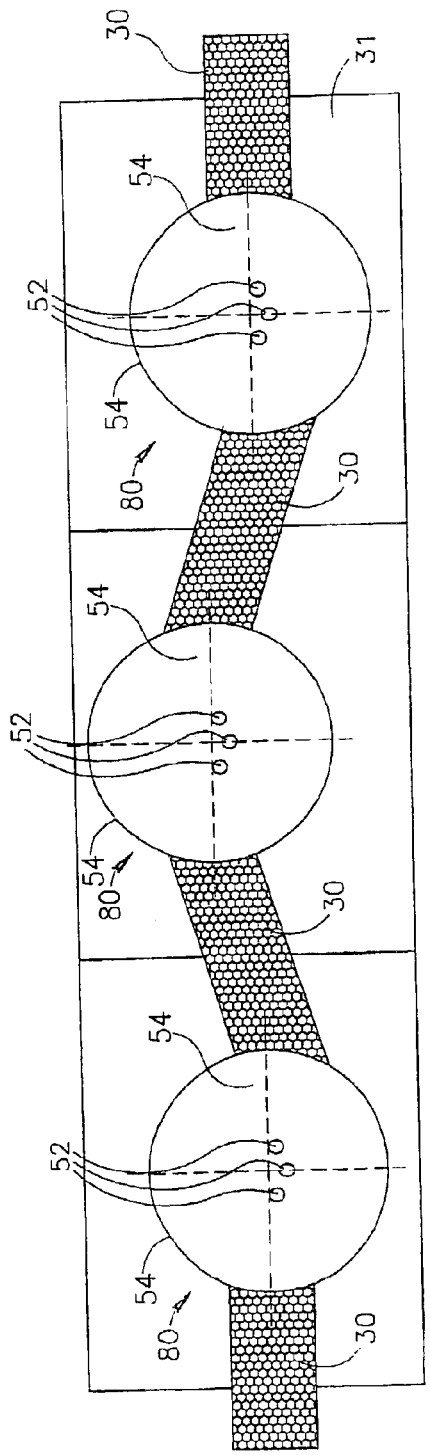
FIG.18A
FIG.18B

SYSTEM AND METHOD FOR DETECTION OF MOTION

This application claims benefit of 60/349,385 filled Jan. 22, 2002.

FIELD OF THE INVENTION

The present invention relates to the field of vibration detection. More particularly, the present invention relates to a system and method for detecting and monitoring of motion using an acoustic (e.g. ultrasound) based scanning system having Doppler-shift detection capabilities.

BACKGROUND OF THE INVENTION

Detection and measurement of motion in the human body has been conducted based on Doppler shift phenomenon using ultrasound techniques. An ultrasonic Doppler detection apparatus operates by transmitting an ultrasonic-wave pulse having a known frequency into the human body at predetermined intervals. A reflected signal, such as an echo signal, from a moving reflective object, such as a blood corpuscle is then received. The phase shift i.e., Doppler shift, between the transmitted and received signal indicates motion velocity.

Blood flow in the small blood vessels is an indication of the regulation of the metabolic, hemodynamic and thermal states of an individual. Thus, there are many situations in routine clinical medicine where measurements of blood flow are useful. Ultrasound equipment used for blood flow detection based on Doppler effect is disclosed in U.S. Pat. Nos. 4,534,357, and 5,035,245.

The measurement of blood flow can generally be done only by health professionals or those with substantial medical training. For example, it is rather difficult to properly orient and position the ultrasound transducer on the patient corresponding to the desired location where blood flow is to be monitored. This is because these devices typically employ ultrasonic waves that are transmitted from and received by the device in a "straight line" manner, meaning the transmitting and receiving waves are parallel to each other. U.S. Pat. No. 5,680,865 discloses an ultrasound probe for use in medical examinations to obtain information on in-vivo motion and specifically on blood flow, capable of scanning a region of interest. The scanning is achieved by employing an electric motor for driving the Doppler ultrasound transducer into the target position.

SUMMARY OF THE INVENTION

According to some embodiments of the present invention, there is provided a device and method for the detection of motion Based on the Doppler effect. According to embodiments of the present invention, a motion detector for detecting motion inside of a body may include a first oscillator to produce an electrical scanning signal and a second oscillator to produce an electrical Doppler signal. A vibrating element may vibrate in response to the scanning and Doppler signals and a vibration transducer may receive vibrations reflected from a structure inside the body. The transducer may convert the reflected vibrations into an electrical signal, and the velocity of the structure from which the vibrations are reflected may be estimated by comparing the frequencies of the transmitted and reflected vibrations.

According to some embodiments of the present invention, a vibrating element may include piezo-ceramic material, and a vibration transducer may include piezo-ceramic material.

According to some embodiments of the present invention, the vibrating element and the vibration transducer may form a single transducer.

As part of some embodiment of the present invention, an apparatus for transmitting and receiving waves may include a processor, at least one piezo-ceramic transceiver in communication with the processor, wherein the piezo-ceramic transceiver may be configured to transmit and receive mechanical waves to and from an object while vibrating. The processor may include a first oscillator, a second oscillator, and a signal detector. A signal detector may be configured to receive electrical waves from the transceiver and convert the electrical waves to an output signal.

Some embodiments of the present invention may relate to a system for detecting motion comprising at least one piezo-ceramic transceiver and a processor unit in communication with the piezo-ceramic transceiver. The processor unit may comprise a first oscillator configured to enable the transmission of mechanical waves from the piezo-ceramic transceiver to an object, a second oscillator configured for vibrating the piezo-ceramic transceiver and a signal detector for converting electrical waves received from the piezo-ceramic transceiver into an output signal.

Some embodiments of the present invention may also relate to a method for detecting motion comprising the steps of providing at least one piezo-ceramic transceiver for oscillating over a predetermined range of voltages and frequencies and transceiving energy waves, energizing the piezo-ceramic transceiver to create vibrations in the piezo-ceramic transceiver, scanning an object over a range provided by the vibrations and transceiving signals to and from the object corresponding to motion.

In another embodiment of the invention, there may be provided an apparatus for transmitting and receiving waves using a two-block piezo-ceramic transceiver. The two-block piezo-ceramic transceiver may comprise at least one piezo-ceramic transmitter, vibrating element, and at least one piezo-ceramic receiver, vibration transducer. The piezo-ceramic transmitter may be configured to transmit mechanical waves to an object and the piezo-ceramic receiver may be configured to receive mechanical waves reflected from an object. The transmitter and receiver may be in communication with a processor which may include a first oscillator, a second oscillator and a signal detector. The first oscillator may be configured for transmitting electric waves to the piezo-ceramic transmitter so as to detect motion in the object. The second oscillator may be configured for transmitting electric waves to the piezo-ceramic transmitter and the piezo-ceramic receiver so as to vibrate the piezo-ceramic transmitter and the piezo-ceramic receiver. The signal detector may be configured to receive electric waves from the receiver and convert the electrical waves into an output signal.

A system for detecting motion according an embodiment of the invention may include at least one piezo-ceramic transmitter or vibrating element, at least one piezo-ceramic receiver or transducer, and a processor unit in communication with the piezo-ceramic transmitter and the piezo-ceramic receiver. The processor unit include a first oscillator configured to enable the transmission of mechanical waves from the piezo-ceramic transmitter to an object, a second oscillator configured for vibrating the piezo-ceramic transmitter and piezo-ceramic receiver and a signal detector for converting the electrical waves received from the piezo-ceramic receiver into an output signal.

A method for detecting motion according to an embodiment of the invention may include the steps of providing at least one piezo-ceramic transmitter and at least one piezo-ceramic receiver for oscillating over a predetermined range of voltages and frequencies and transceiving energy waves, energizing the piezo-ceramic transmitter to create vibrations in the at least one piezo-ceramic transmitter, energizing the piezo-ceramic receiver to create vibrations in the at least one piezo-ceramic receiver, scanning an object over a range provided by the vibrations, transmitting signals to the object and receiving signals from the object corresponding to motion.

In another embodiment of the invention, an apparatus for transmitting may include a housing unit, at least one piezo-ceramic transceiver for transmitting and receiving signals located within the housing and a processor. The processor may include a first oscillator, a second oscillator, and a signal detector. The first oscillator may be configured to transmit waves to the object so as to detect flow in the object, and the second oscillator may be configured for vibrating the piezo-ceramic transceiver so as to scan a wide area of an object. The signal detector is configured to convert the received waves into an output signal.

In another embodiment of the invention, apparatus for detection of blood flow may include a sticker, at least one piezo-ceramic transceiver for transmitting and receiving signals attached to the sticker and a chip processor. The chip processor may include a first oscillator, a second oscillator and a signal detector. The first oscillator may be configured to transmit waves to the object so as to detect flow in the object and the second oscillator may be configured for vibrating the piezo-ceramic transceiver so as to scan a wide area of an object. The signal detector may be configured to convert the received waves into an output signal.

In a further embodiment of the invention, a piezo-ceramic transceiver for detecting motion is disclosed. The piezo-ceramic transceiver may be configured to transmit and receive mechanical waves to and from an object while vibrating, wherein the vibrations may be achieved due to mechanical waves at the plane of the piezo-ceramic transceiver.

BRIEF DESCRIPTION OF THE DRAWINGS

The present invention will be understood and appreciated more fully from the following detailed description taken in conjunction with the appended drawings in which:

FIGS. 4A–4B are schematic representations of a scanning and receiving range for the single-block piezo-ceramic transceiver unit of FIG. 2, according to some embodiments of the present invention;

FIGS. 5A and 5B are schematic illustrations of a two-block piezo-ceramic transceiver unit according to two configurations according to some embodiments of the present invention;

FIGS. 11A–11B are schematic representations of scanning directions of the two-block piezo-ceramic transmitter of FIG. 5, wherein both transmitter and receiver are configured to vibrate, according to several modes of operation;

FIGS. 18A–18B are illustrations of an apparatus according to a further embodiment of the present invention.

DETAILED DESCRIPTION OF THE PRESENT INVENTION

In the following description, various aspects of the invention will be described. For purposes of explanation, specific configurations and details are set forth in order to provide a thorough understanding of the invention. However, it will also be apparent to one skilled in the art that the invention may be practiced without the specific details presented herein. Furthermore, well known features may be omitted or simplified in order not to obscure the invention.

According to some embodiments of the present invention there is an acoustic or ultrasonic motion detection system which may allow detection of in-vivo motions such as, for example, blood flow detection, heartbeat, fetal motion, fetal heartbeat, etc. Some embodiments of the present invention may detect motion in various sized blood vessels, including small arteries and veins such as those of the face and digits.

Figure 1:
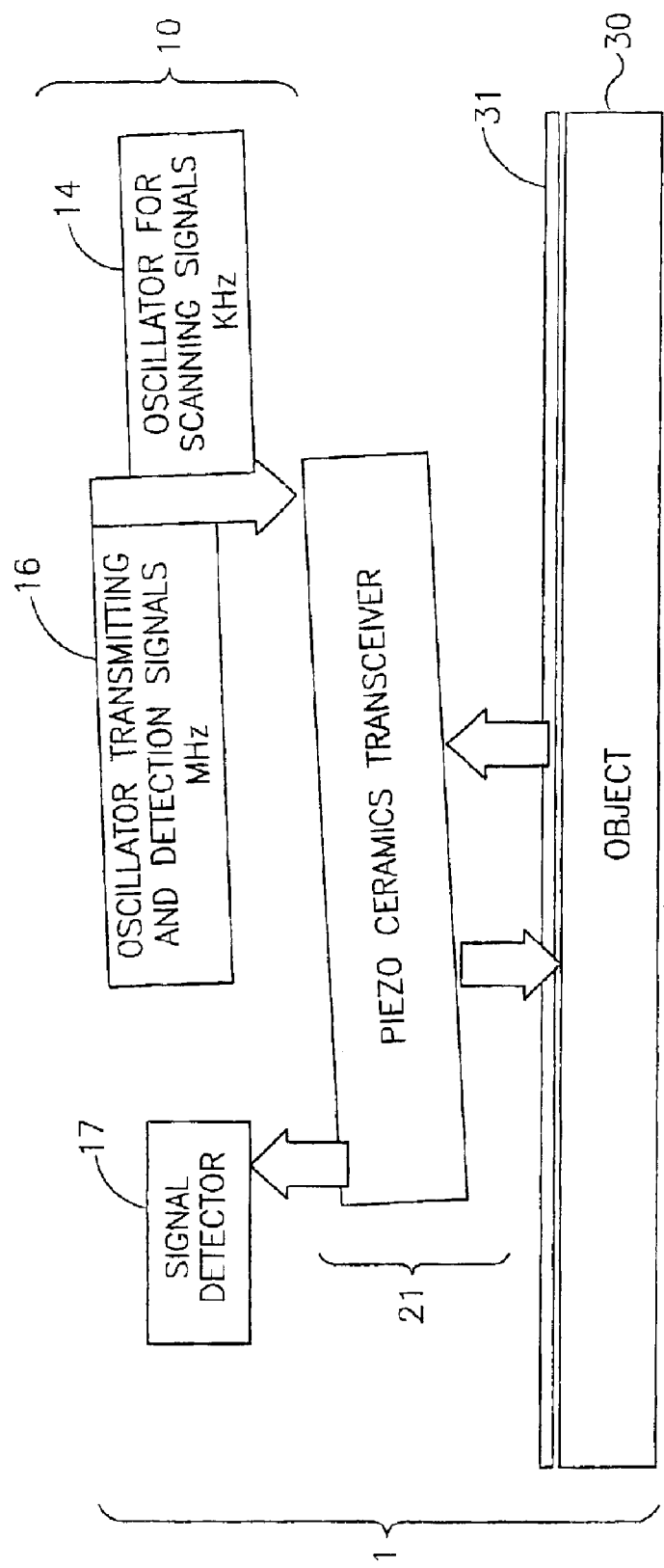
FIG. 1 is a general diagrammatic illustration of a motion monitoring system according to some embodiments of the present invention.

Reference is now made to FIG. 1, which illustrates a motion detection system 1 according to an embodiment of the present invention. System 1 includes a processor 10 and a transceiver 21. Processor 10 may include a first oscillator 16, a second oscillator 14 and a signal detector 17. First oscillator 16 may transmit electrical waves in the Megahertz ("MHz") frequency range to transceiver 21 where the electrical waves are may be transformed into mechanical waves that are transmitted through the thickness of transceiver 21 and through the skin 31, to a target object 30 that may be, for example, an organ, or a blood vessel, etc. The waves may be reflected from target object 30, again passed through transceiver 21, and transformed from mechanical to electrical waves and detected by signal detector 17. Second oscillator 14 may transmit electrical waves in the Kilohertz ("KHz") frequency range to transceiver 21, and the electrical waves may be transformed in transceiver 21 into longitudinal or bending vibration waves that cause planar vibrations (e.g., vibrations in the plane of transceiver 21) within transceiver 21 itself. Processor 10 may include other sets of components.

The use of waves in MHz frequency range may be appropriate for providing diagnosis of one or more parameters of the object. The use of waves in KHz frequency range may increase the scanning area of the transceiver 21, thereby increasing the sensitivity of the transceiver 21. The output signal from the transceiver 21 may simultaneously include a frequency in the MHz frequency range and a frequency in the KHz frequency range. The signal detector may detect the signal in both MHz and KHz frequency ranges and may filter out the KHz frequency component of the signal.

In an embodiment of the invention, object 30 may be a blood vessel, and transmitted MHz vibrations may be reflected from the blood vessel, when a shift in pitch of the acceleration of velocity in moving blood is encountered. The reflected mechanical waves may be transformed back into electrical waves by transceiver 21. Signal detector 17 may receive the transformed electrical waves and the information on the blood flow may be transmitted as an audio or optical signal to the user. Those of ordinary skill in the art may appreciate that any one known conversion method for the conversion of electrical waves to audio or optical signal may be used, for example the transformed electrical waves may be converted to audio using Doppler effect conversion. Other methods may also be used. In other embodiments of the present invention, object 30 may be, for example, a heart of a human fetus, and transmitted MHz vibrations may be reflected from the heart, where a shift in the pitch or frequency of the reflected vibrations may correspond to a change it the velocity of a heart beat or heart beats of a beating heart is encountered.

The use of Doppler shifts of a signal to determine the velocity of an object from which the signal is reflected is well known.

In one embodiment, first oscillator 16 operates alone to transmit waves to object 30. In another embodiment, first oscillator 16 and second oscillator 14 operate together. First oscillator 16 may transmit waves through the thickness of transceiver 21 where the waves are transformed into mechanical waves that are directed to detect motion in object 30. Second oscillator 14 may transmit waves so as to vibrate transceiver 21 in order to achieve a larger scanning and/or receiving area, as will be described more fully hereinbelow.

Figure 2B:
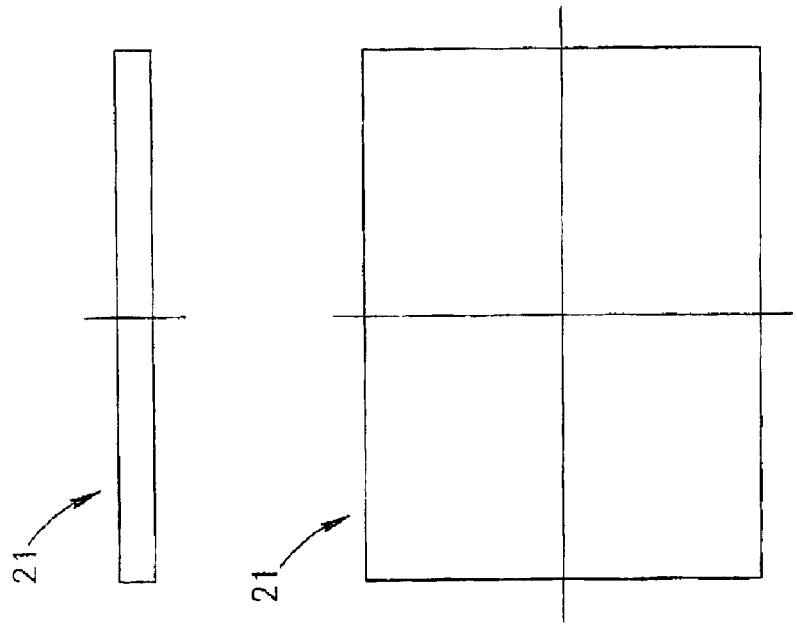
FIGS. 2A and 2B are schematic illustrations of a single-block piezo-ceramic transceiver unit according to two configurations according to some embodiments of the present invention.
Figure 2A:
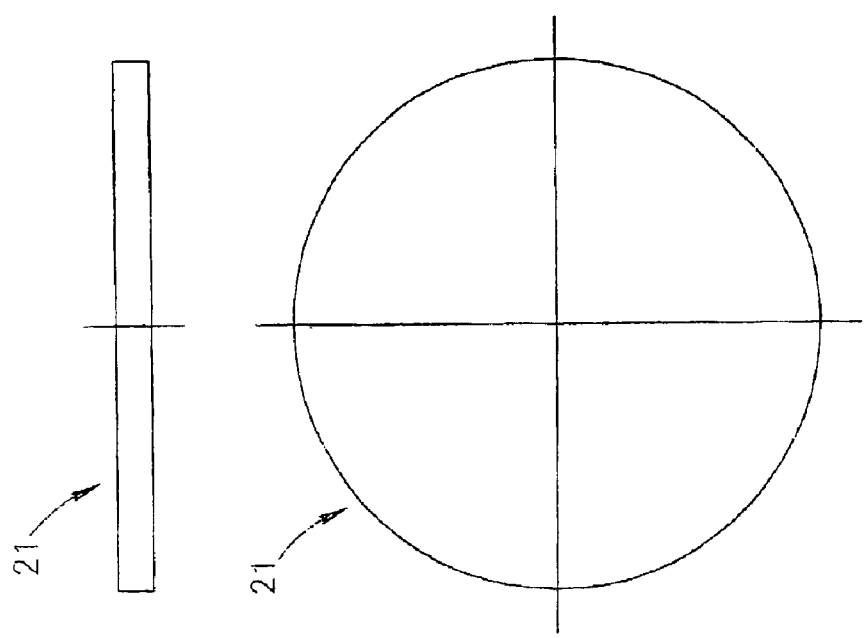

Reference is now made to FIGS. 2A and 2B, which are schematic illustrations of two embodiments of a single-block piezo-ceramic transceiver 21. The transceiver 21 may act as both a vibrating element and a vibration transducer. Single-block piezo-ceramic transceiver 21 may be made from one piece of piezo-ceramic material, which can act as a transceiver, meaning both a transmitter and a receiver. It will be appreciated that transceiver 21 may be made of any other material that is capable of converting electric waves to mechanical waves and mechanical waves to electric waves. In one embodiment, single-block piezo-ceramic transceiver 21 is circular in shape, as shown in FIG. 2A in cross section and in a top view. In another embodiment, single-block piezo-ceramic transceiver 21 is rectangular in shape, as shown in FIG. 2B in cross section and in a top view. It will be appreciated that single-block piezo-ceramic transceiver 21 may be of any shape suitable for transmitting and receiving waves.

Figure 3:
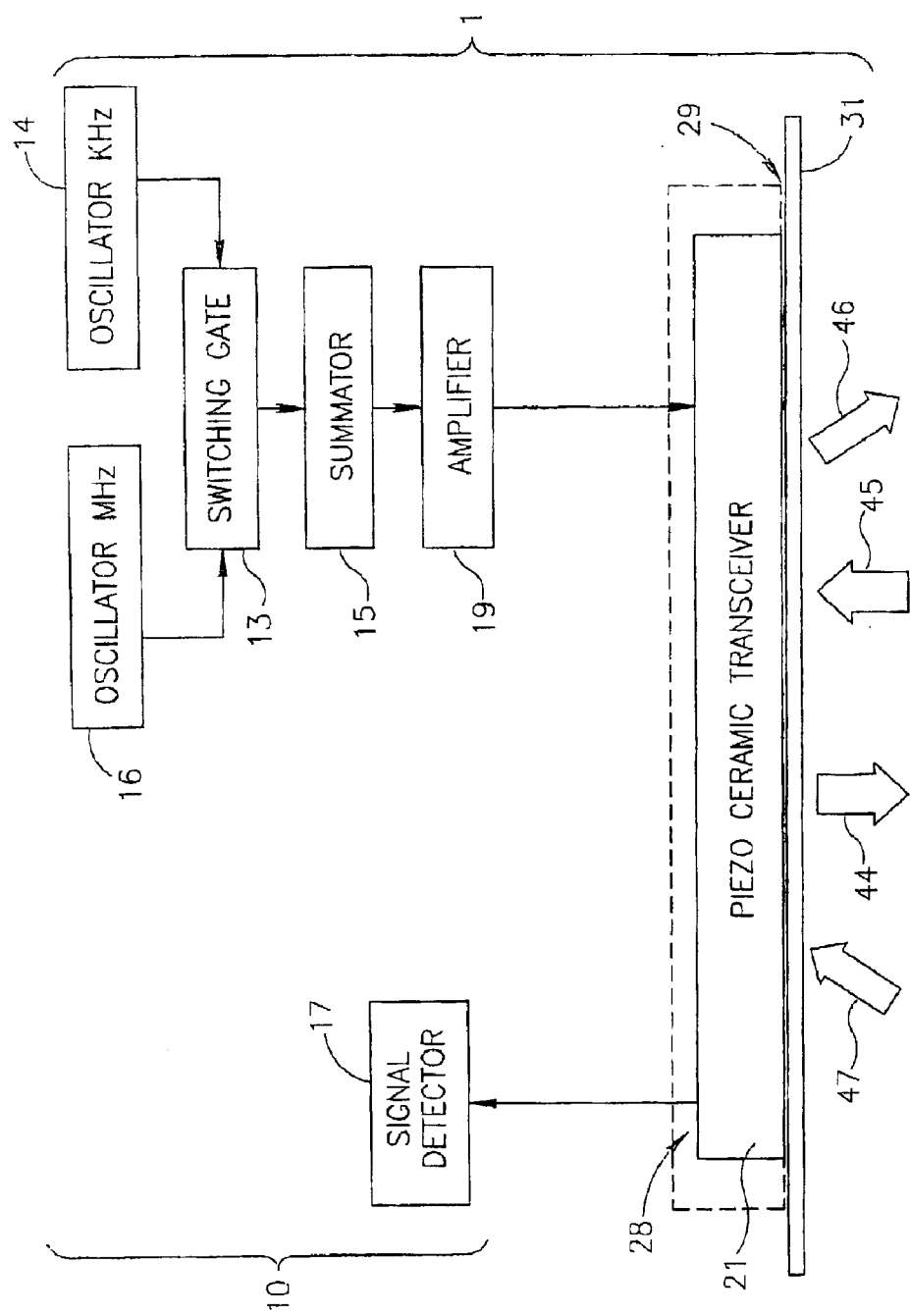
FIG. 3 is a diagrammatic illustrations of a motion monitoring system of having a single-block piezo-ceramic transceiver according to some embodiments of the present invention.

Reference is now made to FIG. 3, which is a block diagram illustration of system 1 showing processor 10 in communication with transceiver 21. Processor 10 may include a first and a second oscillator 16 and 14 respectively, a switching gate 13, summator 15, amplifier 19, and a signal detector 17. First and second oscillators 16 and 14 may be configured to transmit electric waves to transceiver 21, at the MHz and KHz frequencies, respectively. Switching between KHz and MHz frequency waves may be accomplished by switching gate 13. When transmitting both MHz and KHz frequency waves, summator 15 may group the KHz and MHz frequency waves before being amplified by amplifier 19 and transmitted to transceiver 21. The transmission of both MHz and KHz frequency waves may provide scanning capabilities in the KHz frequency range. The use of a signal in the KHz frequency range may increase the surface that may be examined by the transceiver 21.

The single-block piezo-ceramic transceiver 21 may transform the transmitted electrical waves to mechanical waves and reflected received mechanical waves to electrical waves. In some embodiments it may be coated by a, for example, plastic case 28, which may be put in contact with the skin 31. A thin layer of gel 29, such as ultrasound gel may be placed between transceiver 21 and the skin 31. In some embodiments, a transceiver may be packaged with gel like coating already applied to its surface.

The mechanical waves reflected from object 30, may be transformed to electrical waves by a vibration transducer, received and detected by signal detector 17, and processed into an audio or video or optical output signal.

System 1 may function to transmit mechanical waves to an object and receive reflected waves corresponding, for example, to blood motion. This allows the user to locate small blood vessels, determines vessel potency and checks circulation in small blood vessels. One or more parameters of the object may be examined using Doppler effect conversion or any other conversion methods that may allow one to detect the acceleration of velocity of the moving object. The specific MHz frequency range of the acoustical waves transmitted inside the body may be selected in accordance with one or more parameters of the object to be examined. In general, the higher the frequency used, the higher the resolution possible. The user may receive an audio and/or visual signal representative of the object that is examined. The increased sensitivity of the device may allow a more rapid detection and examination of an object to be examined.

Reference is now made to FIG. 4A, which depicts a schematic representation of scanning ranges 41 and 42 of single-block piezo-ceramic transceiver 21 over object 30 when MHz frequency waves are supplied and when MHz and KHz frequency waves are supplied, respectively.

In a first embodiment, for example the embodiment shown in FIG. 3, first oscillator 16 supplies electrical waves in the MHz frequency alone. These electrical waves are transmitted through the thickness of the single-block piezo-ceramic transceiver 21. Thus, the mechanical waves transmitted to object 30 are approximately perpendicular to single-block piezo-ceramic transceiver 21 as depicted by arrows 44, and the scanning range of object 30 is as depicted by line 41.

In another embodiment, for example the embodiment shown in FIG. 3, first and second oscillators 16 and 14 supply electrical waves in the MHz and KHz frequencies. The KHz frequency waves cause vibrations in single-block piezo-ceramic transceiver 21. In one embodiment KHz frequency waves that cause vibrations in the piezo-ceramic transceiver supplied to the transceiver at the same time that MHz frequency waves are transmitted from single-block piezo-ceramic transceiver 21 to target object 30. Thus, MHz mechanical waves are transmitted at various angles as depicted by arrows 46. When the waves are transmitted at various angles, the scanned area of the object is typically increased as depicted by line 42.

In another embodiment KHz frequency waves that cause vibrations in piezo-ceramic transceiver 21 are supplied while the transceiver is receiving mechanical waves from object 30. In another embodiment KHz frequency waves that cause vibrations in piezo-ceramic transceiver 21 are supplied continuously while transmitting MHz frequency waves and while receiving mechanical waves from object 30.

Reference is now made to FIG. 4B, which depicts a schematic representation of the effective receiving ranges 41 and 42 of single-block piezo-ceramic transceiver 21 over object 30 when MHz frequency waves are supplied and when MHz and KHz frequency waves are supplied, respectively. The effective receiving range, e.g., the range where a readable electrical signal is achieved, is obtained when the waves hit the piezo-ceramic transceiver at a range of angles of approximately between 50–120 degrees. The most effective signal is typically achieved when the wave hits perpendicularly to the piezo-ceramic transceiver.

Waves depicted by arrows 47 are reflected from object 30 to single-block piezo-ceramic transceiver 21. When single-block piezo-ceramic transceiver 21 is not vibrating, receiving waves, depicted by arrows 47, hit single-block piezo-ceramic transceiver 21 at an angle A which is greater than 120-degrees. When single-block piezo-ceramic transceiver 21 is vibrating, waves, depicted by arrows 47, hit single-block piezo-ceramic transceiver 21 at an angle B, which is 50–120 degrees. In one embodiment, only waves hitting single-block piezo-ceramic transceiver 21 at angles approximately in the range of 50–120 degrees are effectively detected by signal detector 17. In other embodiments, other angles may be effective.

Typically, the scanned area of object 30 is broader when single-block piezo-ceramic transceiver 21 is vibrating, as shown by lines 41 and 42. Further, the intensity of the received signals is higher when single-block piezo-ceramic transceiver 21 is vibrating, since a greater number of received waves are effective, as compared to the number of effective waves received when single-block piezo-ceramic transceiver 21 is not vibrating.

The frequency of the planar vibrations in single-block piezo-ceramic transceiver 21 is typically in the range of 20–100 KHz (non-audible). In one embodiment, the frequency is 85 KHz as supplied by second oscillator 14. First oscillator 16 provides an alternating current at a frequency range of 1–10 MHz. In one embodiment, the frequency is 2.5 MHz The waves applied may be of running or standing types, and can be applied in bursts. Other frequencies and types of waves may be used.

In another embodiment of the invention, a two-block piezo-ceramic transceiver is introduced. Reference is now made to FIGS. 5A–5B, which are schematic illustrations of a two-block piezo-ceramic transceiver 22. It will be appreciated that two-block piezo-ceramic transceiver 22 may be made of any other material that is capable of converting electric waves to mechanical waves. Two-block piezo-ceramic transceiver 22 is comprised of a piezo-ceramic transmitter 23 and a piezo-ceramic receiver 24. In one embodiment, transmitter 23 and receiver 24 are half-circular in shape, as shown in FIG. 5A in cross section and in a top view. In another embodiment, transmitter 23 and receiver 24 are rectangular in shape, as shown in FIG. 5B in cross section and in a top view. It will be appreciated that transmitter 23 and receiver 24 may be configured in any shape for transmitting and receiving waves.

Figure 6:
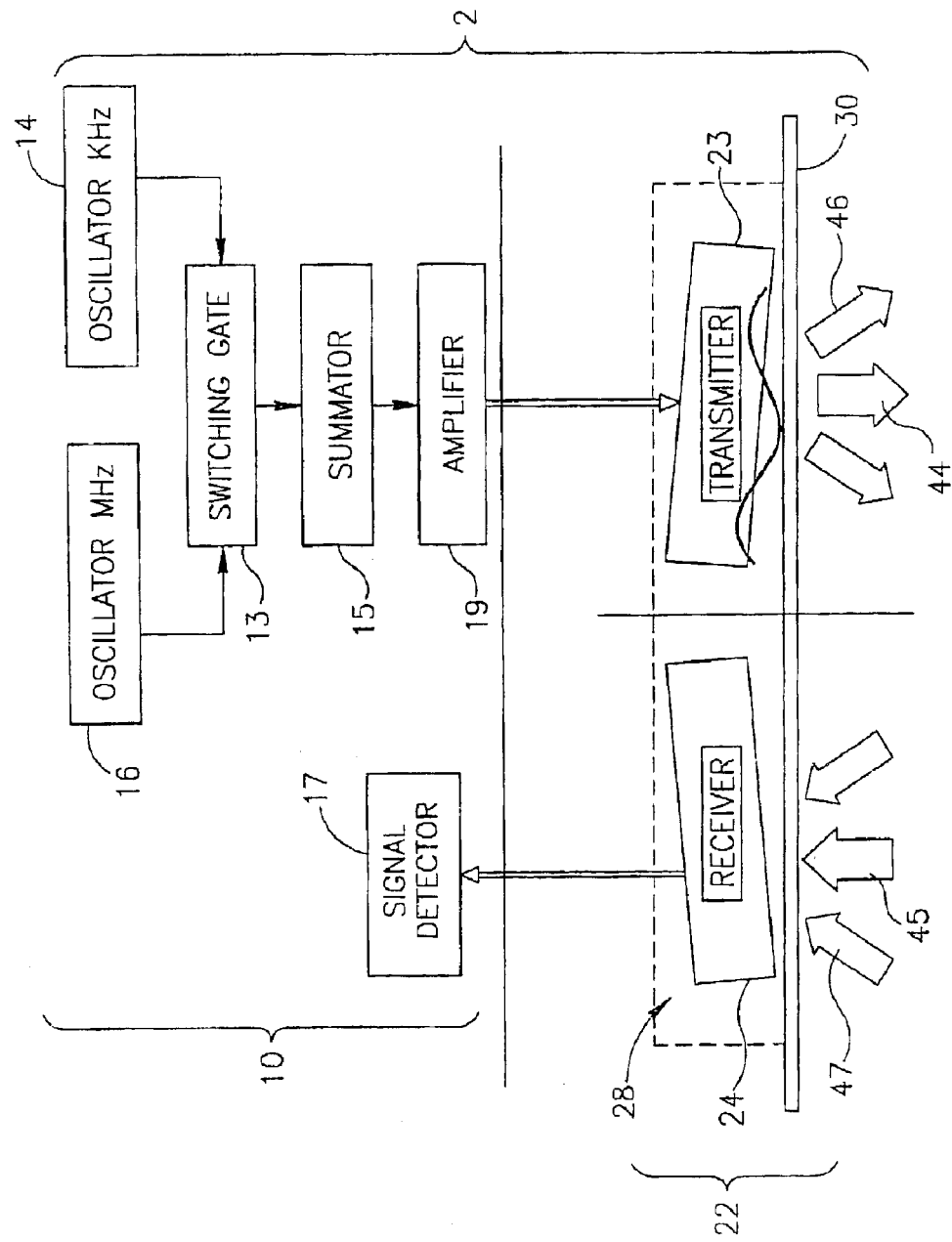
FIG. 6 is a diagrammatic illustration of the motion monitoring system of FIG. 1 having the two-block piezo-ceramic transceiver of FIG. 5, according to according to some embodiments of the present invention, wherein the transmitter is configured to vibrate.

Reference is now made to FIG. 6, which is a block diagram illustration of system 2 for continuous scanning. System 2 includes a processor 10 in communication with two-block piezo-ceramic transceiver 22. Two-block piezo-ceramic transceiver 22 includes transmitter 23 and receiver 24 situated next to each other in plastic case 28. In one embodiment, transmitter 23 may vibrate while receiver 24 is not vibrating. Processor 10 may include first and second oscillators 16 and 14, a switching gate 13, summator 15, amplifier 19, and a signal detector 17. First and second oscillators 16 and 14 are configured to transmit electric waves to transmitter 23, at the MHz and KHz frequencies, respectively. Switching between KHz and MHz frequency waves is accomplished by switching gate 13. When transmitting both MHz and KHz frequency waves, summator 15 groups the KHz and MHz frequency waves before amplified by amplifier 19 and transmitted to transmitter 23. Processor 10 may include other sets of components.

System 2 locates and monitors motion by the placement of transmitter 23 and receiver 24 over object 30 and scanning the area with Doppler ultrasound using transmitter 23. First oscillator 16 provides MHz electrical waves that cause scanning to occur, in combination with second oscillator 14, which provides KHz electrical waves that cause vibrations in transmitter 23.

The electrical waves are transformed by transmitter 23 into scanning and vibrating mechanical waves. The vibrating mechanical waves are designed to vibrate transmitter 23 in a specific mode of planar vibrations. Thus, the scanning waves as depicted by arrows 46 can be transmitted in various directions, achieving a wide angle of scanning as described above in FIG. 4A.

The transmitted scanning mechanical waves 46 are reflected from object 30 when a shift in pitch from, for example, moving blood, heartbeat, etc. is encountered. They are reflected as mechanical waves, and are transformed into electrical waves by receiver 24. In an embodiment where receiver 24 is not configured to vibrate in the described embodiment, only waves within the angle range of approximately 50–120 degrees, as depicted by arrow 47, can be effectively received by receiver 24 where they are transformed into electrical waves. Signal detector 17 receives the electrical waves and they are then processed into an audio and/or optical output. Other angles may be used.

Reference is now made to FIGS. 7A–7D, which depict schematic representations of scanning ranges of transmitter 23 in different modes of planar vibration. Waves in the MHz range are transmitted in various directions as transmitter 23 vibrates, as shown by arrows 44 and 46. Reflected waves are received at receiver 24, at angles depicted by arrows 45 and 47. Other modes of scanning ranges may be used.

Figure 7A:
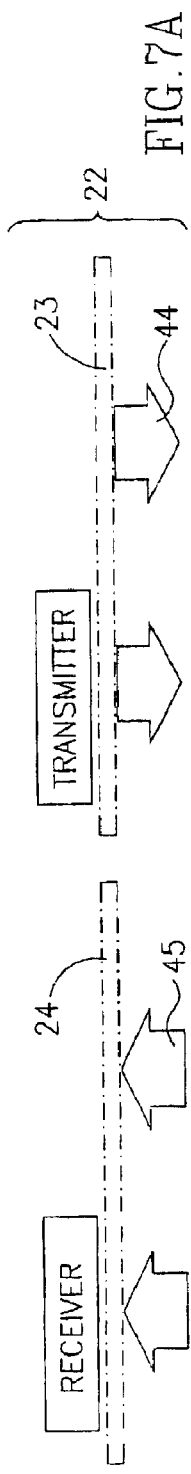
FIGS. 7A–7D are schematic representations of scanning directions of the two-block piezo-ceramic transceiver of FIG. 5, wherein the transmitter is configured to vibrate, according to several modes of operation.
Figure 7B:
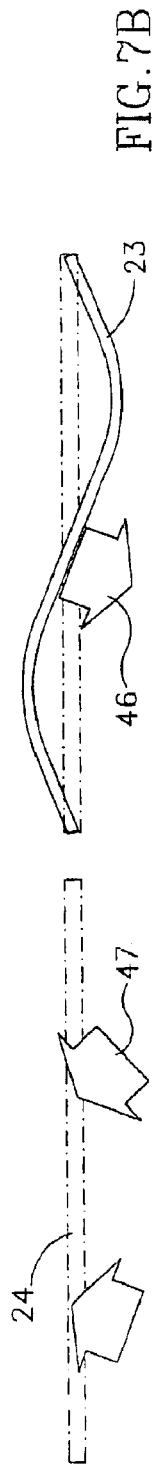
Figure 7C:
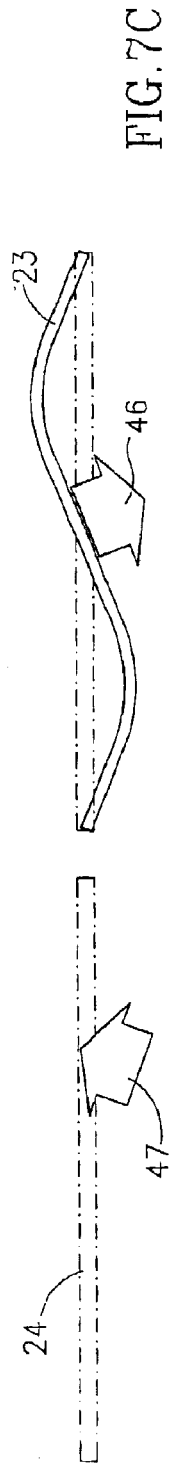
Figure 7D:
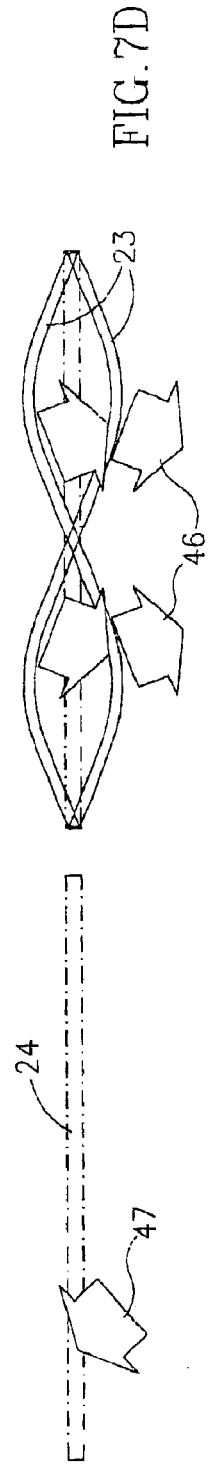

FIG. 7A shows transmitter 23 transmitting waves without vibrating. Thus, the wave transmission is essentially unidirectional in a direction typically approximately perpendicular to the transmitter 23 as depicted by arrow 44. FIGS. 7B and 7C shows transmitter 23 vibrating in a first mode of vibration and FIG. 7D shows transmitter 23 vibrating in a second mode of vibration. Thus the waves are transmitted in various directions as depicted by arrow 46, allowing for a wider range of scanning.

Other modes of vibration may be used. Second mode of vibration was described hereinabove in order to clarify some embodiments of the present invention. However, it should be noted that the present invention is not limited to such modes of vibration and that other suitable modes of vibration may be used. For example, according to further embodiments of the present invention, the transceiver 21 may be capable of vibrating in any mode that is physically possible. Those of ordinary skill in the art, may appreciate that the shape of the piezo-ceramic element and the connection points of the piezo-ceramic element and/or other parameters associated with the piezo-ceramic element may affect the mode of vibration. The various modes of vibration may allow the creation of a wide range of angular orientations of transmitted mechanical waves from transmitter 23.

Figure 8:
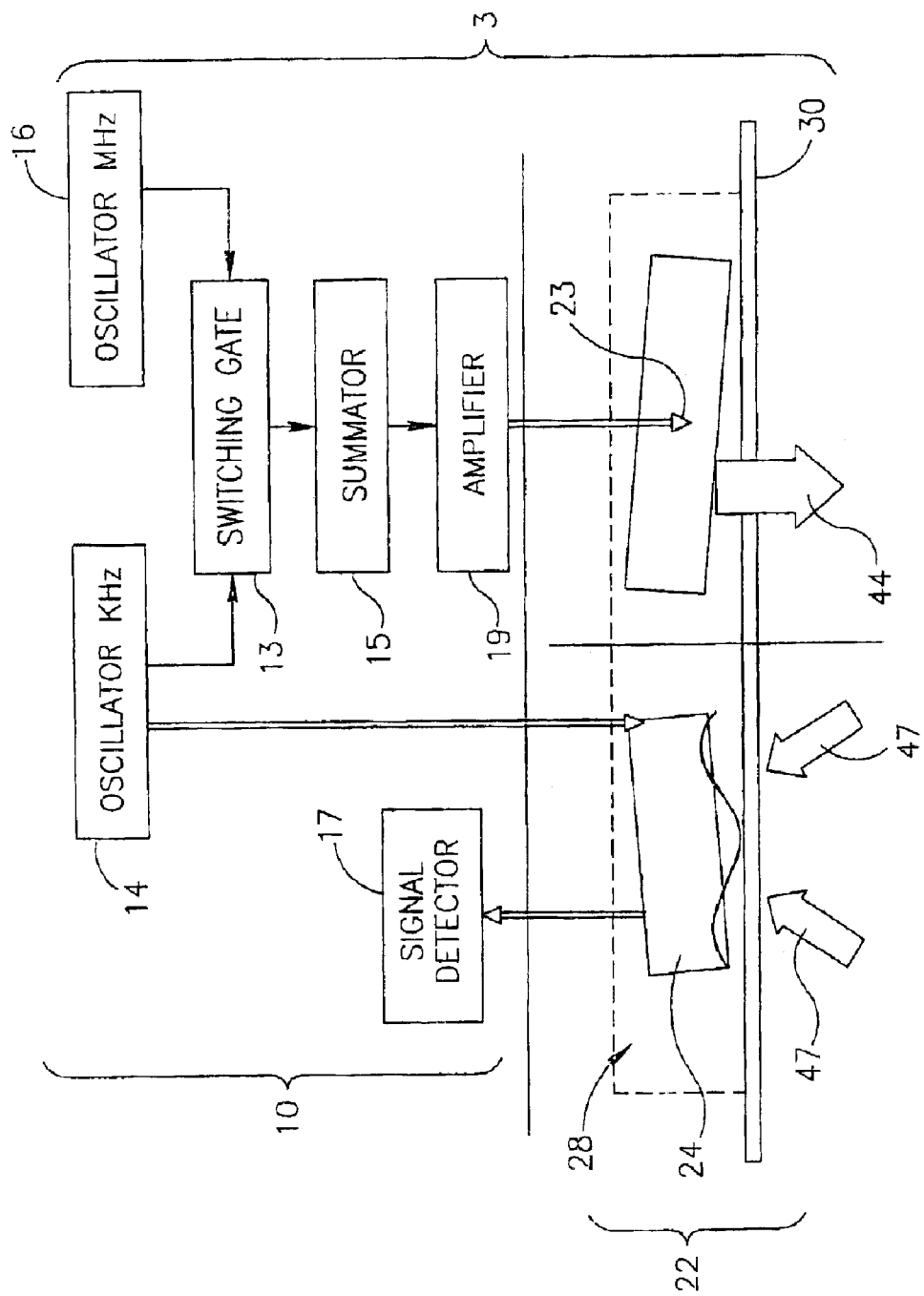
FIG. 8 is a diagrammatic illustration of the motion monitoring system of FIG. 1 comprising the two-block piezo-ceramic transceiver of FIG. 5, according to some embodiments of the present invention, wherein the receiver is configured to vibrate.

Reference is now made to FIG. 8, which is a block diagram illustration of system 3 for continuous scanning. System 3 includes processor 10 in communication with two block piezo-ceramic transceiver 22, according to one embodiment of the present invention wherein two-block piezo-ceramic transceiver 22 includes transmitter 23 and receiver 24, typically situated next to each other in plastic case 28. Processor 10 may include first and second oscillators 16 and 14, a switching gate 13, summator 15, amplifier 19, and a signal detector 17. First and second oscillators 16 and 14 are configured to transmit electric waves to transmitter 23, at the MHz and KHz frequencies, respectively and second oscillator 14 is configured to transmit electric waves to receiver 24 at the KHz frequency.

The receiver 24 may receives an electrical signal in the KHz range. In response, the receiver may oscillate. The oscillation of the receiver may produce planar vibrations. The planar vibrations of the receiver 24 may allow the receiver 24 to receive a signal from multiple directions.

Switching between KHz and MHz frequency waves may be accomplished by, for example, switching gate 13. When transmitting both MHz and KHz frequency waves to transmitter 23, summator 15 groups the KHz and MHz frequency waves before amplified by amplifier 19 and transmitted to transmitter 23. Oscillator 14 may transmit KHz frequency waves alone to receiver 24. Processor 10 may include other sets of components.

In one embodiment, transmitter 23 is not configured to vibrate, while receiver 24 may vibrate, thus MHz frequency waves are transmitted from oscillator 16 to transmitter 23 and KHz frequency waves are transmitted from oscillator 14 to receiver 24.

System 3 locates and monitors motion for example, vascular flow, by the placement of transmitter 23 and receiver 24 over object 30 and scanning the area with Doppler ultrasound using transmitter 23. First oscillator 16 provides MHz electrical waves that cause scanning to occur to transmitter 23, and second oscillator 14, provides KHz electrical waves that cause vibrations, to receiver 24.

Typically, the transmitted scanning mechanical waves 44 are transmitted only in a direction approximately perpendicular to transmitter 23. Mechanical waves are reflected from object 30 when they encounter a shift in pitch corresponding to a change it the velocity of the moving blood, and are then transformed into electrical waves by the receiver 24. Second oscillator 14 supplies KHz frequency electrical waves in a specific mode of planar vibration, which causes receiver 24 to vibrate. Thus, the reflected waves as depicted by arrow 47, are received from a larger scanning area of object 30 and at a higher intensity as described above with reference to FIG. 4.

Figure 9:
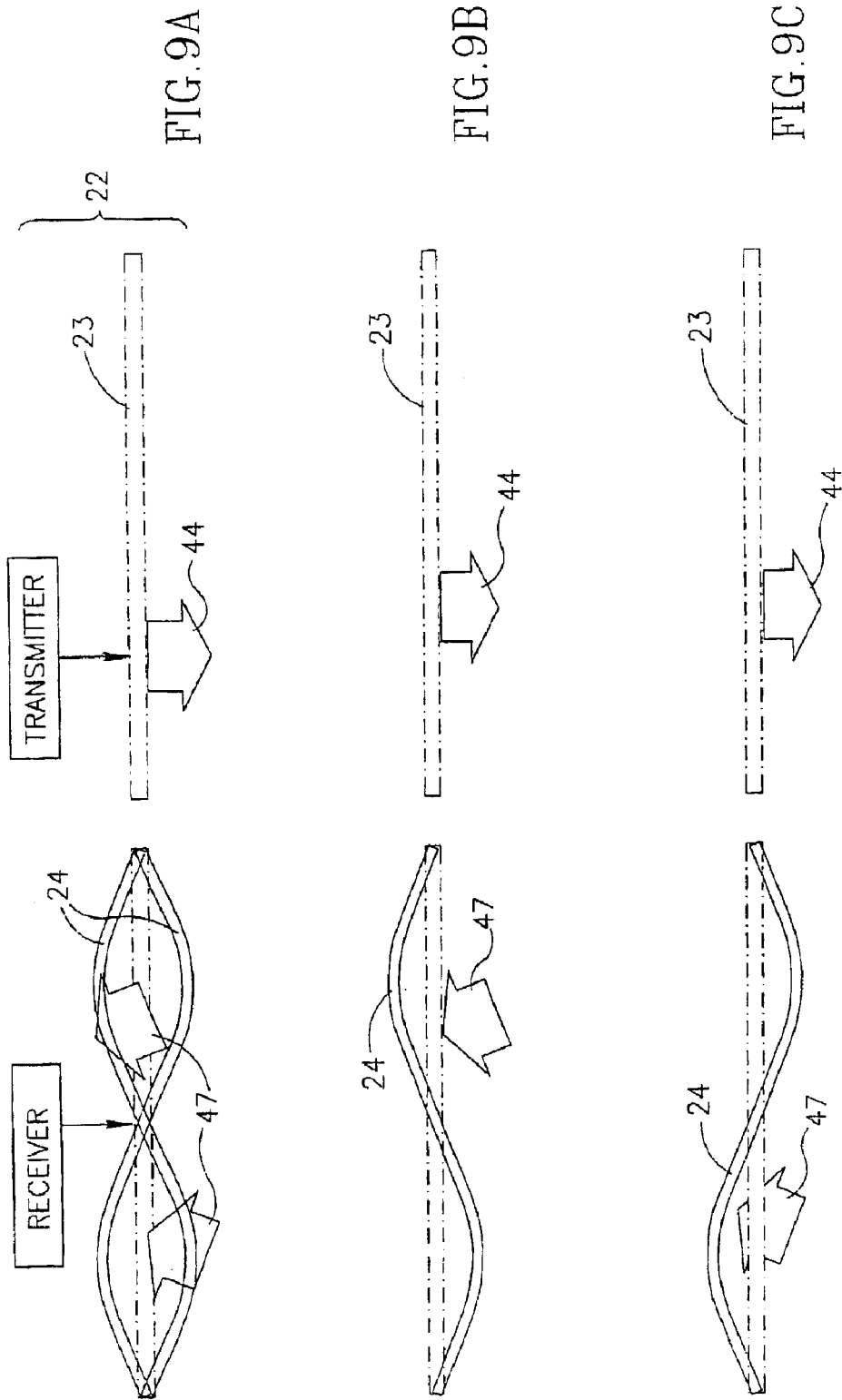
FIGS. 9A–9C are schematic representations of scanning directions of the two-block piezo-ceramic transceiver of FIG. 5, wherein the receiver is configured to vibrate, according to several modes of operation.

Reference is now made to FIGS. 9A–9C, which depict schematic representations of scanning ranges of receiver 24 in different modes of vibration. In the embodiment shown in FIGS. 9A–9C, transmitter 23 is not vibrating, and receiver 24 vibrates and receives reflected waves, as shown by arrows 47. Receiver 24 can receive waves while vibrating in the second mode of vibration, as shown in FIGS. 9A, 9B and 9C. Thus, in one embodiment, receiver 24 is configured to receive waves without vibrating. In another embodiment, receiver 24 is configured to receive waves while vibrating in a first mode of vibration. Further embodiments of the present invention, may include the possibility of vibrating in any mode of planar vibration, up to what is physically possible.

Since, typically, the clearest signals are received perpendicular to receiver 24, by vibrating receiver 24, thus increasing the scanning range, the number of clear signals is increased since more signals have a chance of hitting receiver 24 perpendicular to the plane of reception.

Figure 10:
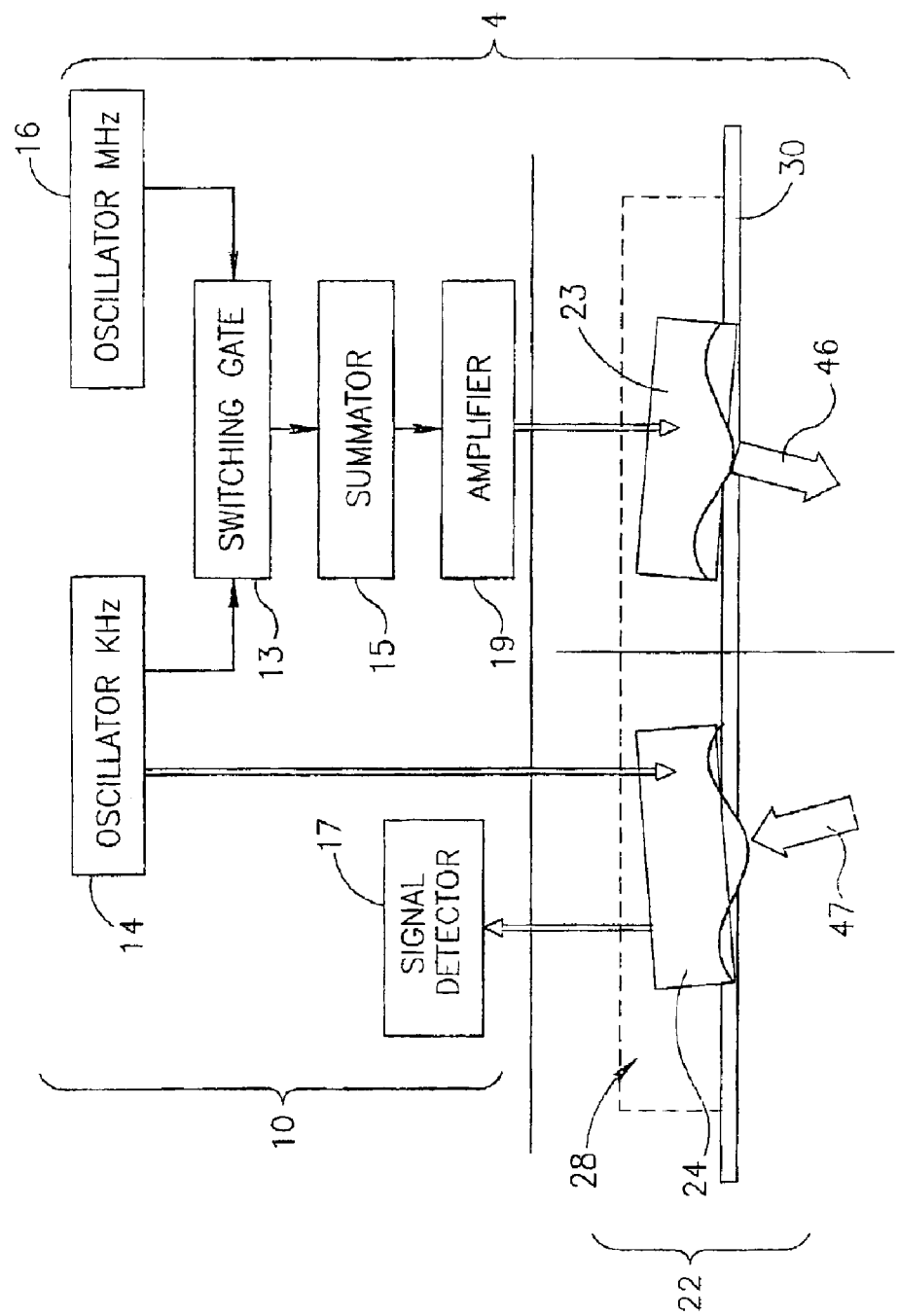
FIG. 10 is a diagrammatic illustration of the motion monitoring system of FIG. 1 comprising the two-block piezo-ceramic transceiver of FIG. 5, according to another embodiment of the present invention, wherein both transmitter and receiver are configured to vibrate.

Reference is now made to FIG. 10, which is a block diagram illustration of system 4 for continuous scanning. System 4 includes processor 10 in communication with two block piezo-ceramic transceiver 22, according to one embodiment of the present invention. Two-block piezo-ceramic transceiver 22 includes transmitter 23 and receiver 24 situated next to each other as two separate piezo-ceramic pieces. In the embodiment illustrated in FIG. 10, both transmitter 23 and receiver 24 may vibrate. Processor 10 may include other sets of components.

Processor 10 may include first and second oscillators 16 and 14, a switching gate 13, summator 15, amplifier 19, and a signal detector 17. First and second oscillators 16 and 14 are configured to transmit electric waves to transmitter 23, at the MHz and KHz frequencies, respectively and second oscillator 14 is configured to transmit electric waves to receiver 24 at the KHz frequency. Switching between KHz and MHz frequency waves is accomplished by switching gate 13. When transmitting both MHz and KHz frequency waves to transmitter 23, summator 15 groups the KHz and MHz frequency waves before amplified by amplifier 19 and transmitted to transmitter 23. Oscillator 14 may transmit KHz frequency waves alone to receiver 24.

System 4 locates and monitors, for example, vascular flow by the placement of transmitter 23 and receiver 24 over object 30 and scanning the area with Doppler ultrasound using transmitter 23. First oscillator 16 provides MHz electrical waves that cause detecting to occur, to transmitter 23, in combination with second oscillator 14, which provides KHz electrical waves that cause vibrations and scanning to transmitter 23. The electric waves are transformed by the transmitter into scanning mechanical waves and vibrating mechanical waves substantially simultaneously. Second oscillator 14 further supplies KHz electric waves to receiver 24, these electric waves transformed by receiver 24 to mechanical waves that cause vibrations in receiver 24.

The vibrating mechanical waves are designed to vibrate transmitter 23 and receiver 24 in a specific mode of vibrations, causing scanning waves to be transmitted in various directions, as depicted by arrow 46. Thus, a wide scanning angle is achieved, as described above for FIG. 4A.

Waves 46 are reflected from the object 30 as mechanical waves when they encounter a shift in pitch from moving blood, and are transformed by receiver 24 into electrical waves. Receiver 24 also vibrates, as a result of the KHz frequency electrical waves supplied by oscillator 14, in a specific mode of vibrations. Thus the reflecting waves as depicted by arrow 47 are received from a larger scanning area of object 30 and at a higher intensity as described above for FIG. 4B.

Reference is now made to FIGS. 11A–11B, which depict schematic representations of scanning ranges of transmitter 23 and receiver 24 in different modes of vibration.

FIGS. 11A and 11B show transmitter 23 and receiver 24 vibrating in a second mode of vibration. Illustration of the difference between phase of vibration of transmitter 23 and receiver 24. Thus the waves are may be transmitted and may be received in various directions as depicted by arrows 46 and 47 respectively. Further embodiments include the possibility of vibrating together or separately in any mode, up to what is physically possible. For example, transmitter 23 vibrating in first mode and receiver 24 vibrating in second mode, other modes may be applied.

Figure 12A:
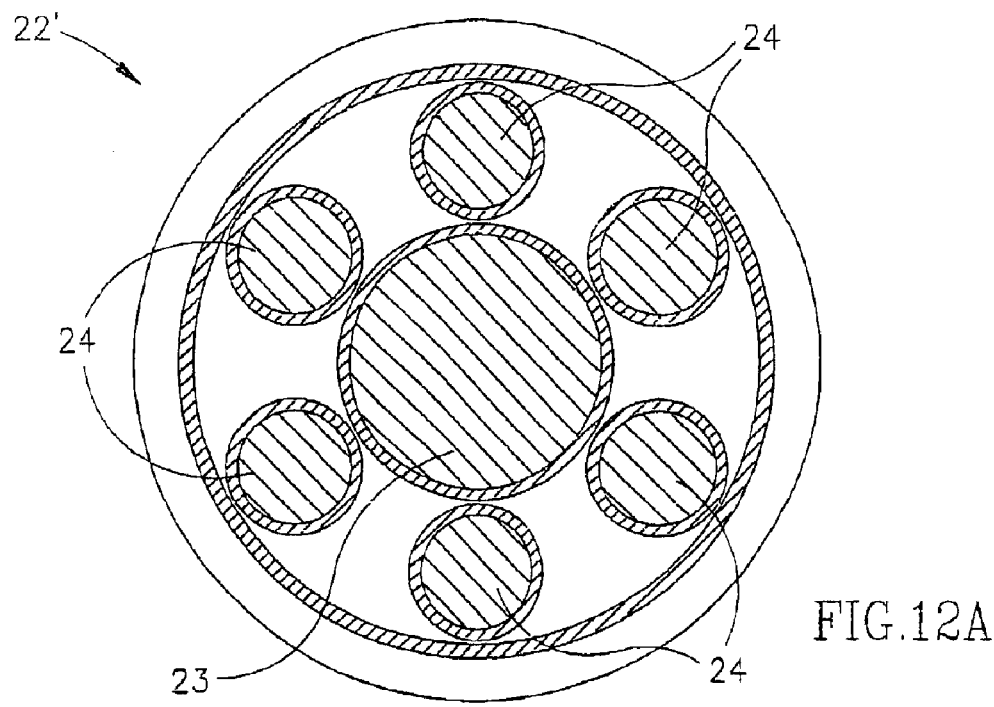
FIGS. 12A–12C are schematic illustrations of a multi-block piezo-ceramic transceiver unit according to three configurations.
Figure 12B:
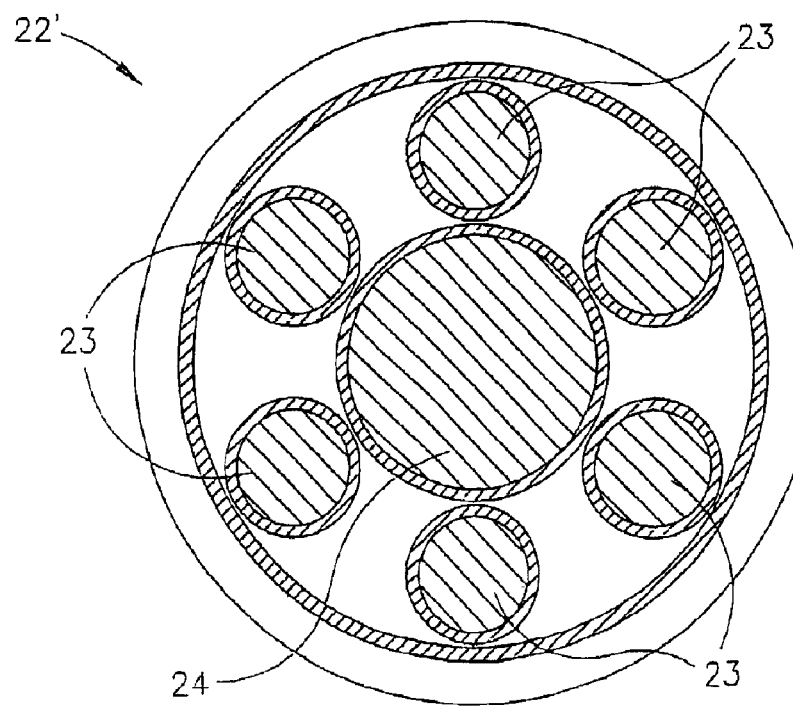
Figure 12C:
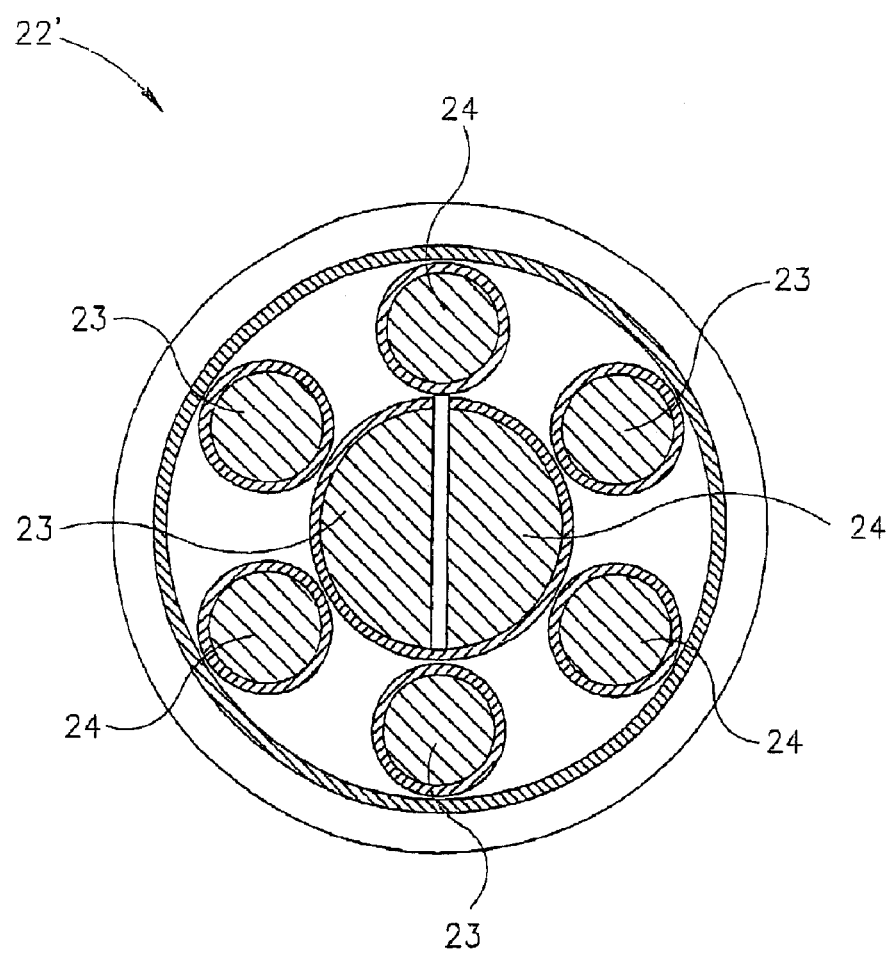

Reference is now made to FIGS. 12A–12C, which are schematic illustrations of a multi-block piezo-ceramic transceiver unit 22 according to three different configurations. Configurations other than those shown are possible. FIG. 12A illustrates a configuration of the multi-block piezo-ceramic transceiver unit 22 including one circular transmitter 23 and several circular receivers 24 situated around transmitter 23. FIG. 12B illustrates a configuration of the multi-block piezo-ceramic transceiver unit 22 including one circular receiver 24 and several circular transmitters 23 situated around receiver 24. FIG. 12C illustrates a configuration of the multi-block piezo-ceramic transceiver unit 22 including one circular two-block D-shaped piezo-ceramic transceiver 22 wherein half circle may be the transmitter and half may be the receiver surrounded by circular transmitters 23 and circular receivers 24. It will be appreciated that any configuration of the multi-block piezo-ceramic transceiver compatible for transmitting and receiving waves can be applied. Transmitters 23 and receivers 24 may be adapted to vibrate in the KHz and in the MHz frequency ranges. Thus, the scanning area and the sensitivity of device may be increased. Scanning may be achieved by switching between transmitters 23 alternately or between transmitters 23 and receivers 24 alternately. Transmitters 23 and receivers 24 may be of any suitable shape, for example, as was illustrated in FIGS. 2A, 2B, 5A and 5B. According to one embodiments of the present invention, in case a desired signal quality is obtained the transmitter may be instructed to operate in closed loop mode, such that the scanning may be discontinued.

Figure 13:
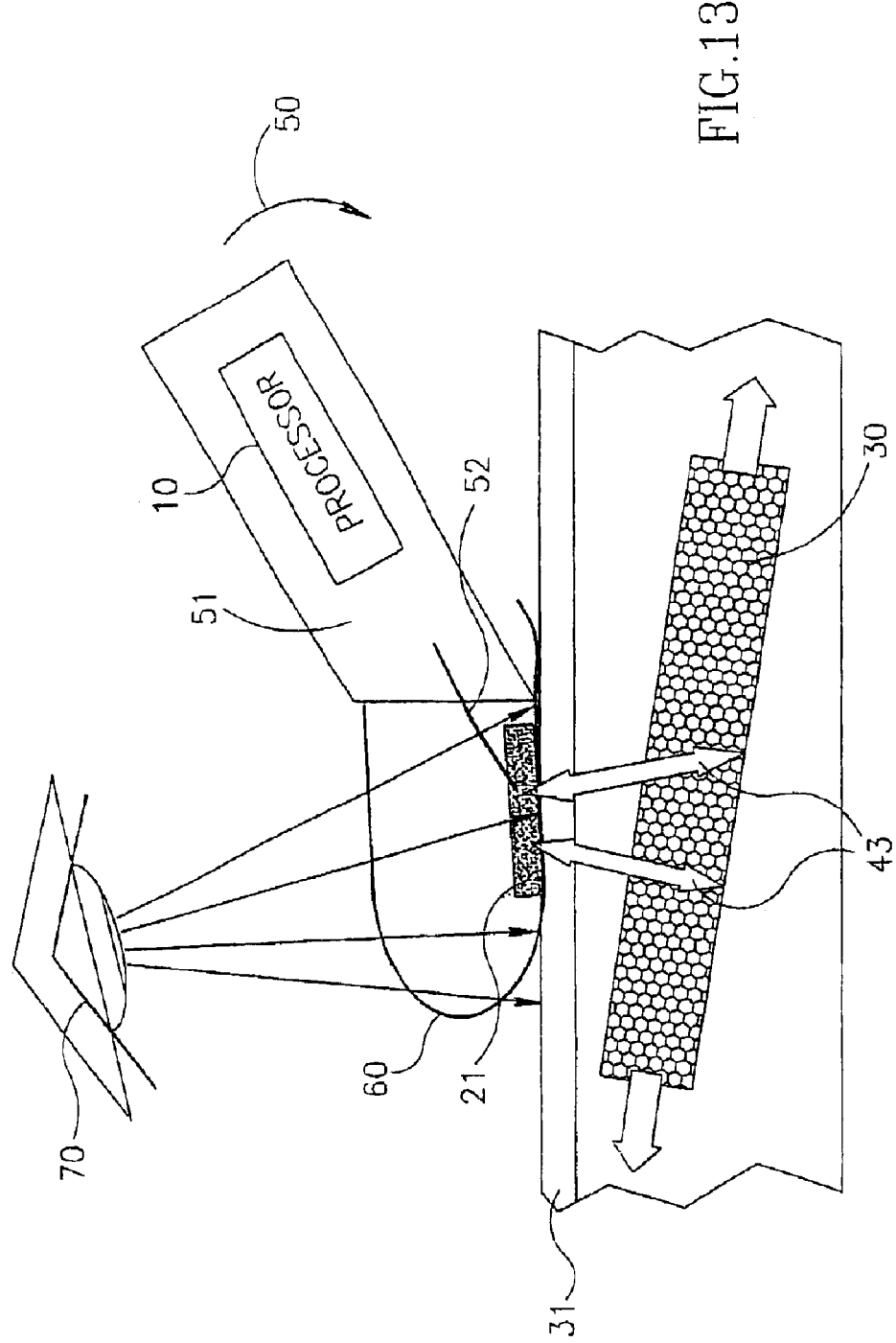
FIG. 13 is an illustration of an apparatus according to one embodiment of the present invention.

Reference is now made to FIG. 13, which is an illustration of apparatus 50 for vascular flow detection, according to one embodiment of the invention. Apparatus 50 includes a handle 51 with processor 10 inside and housing 60. Housing 60 may include single-block, two-block or multi block piezo-ceramic (for example, as illustrated in FIG. 2, 5 or 12) transceiver within it. Transceiver 21 is connected to processor 10, located within handle 51 by a wire connection 52. The portion of housing 60 with transceiver unit 21 may be placed against the skin 31 over scanned object 30, which, in one embodiment, is a blood vessel. Waves 43 from apparatus 50 penetrate the skin and reach at least one portion of a blood vessel so that blood flow can be detected. According to one embodiment, housing 60 is transparent, allowing the user to see the area of skin on which it is placed, as illustrated with an eye 70 viewing apparatus 50. Those of ordinary skill in the art may appreciate the applicability of sensitivity increment to apparatus 50. Sensitivity increment was discussed in greater detail hereinabove and may be applied to the discussion of the present embodiment.

Figure 14A:
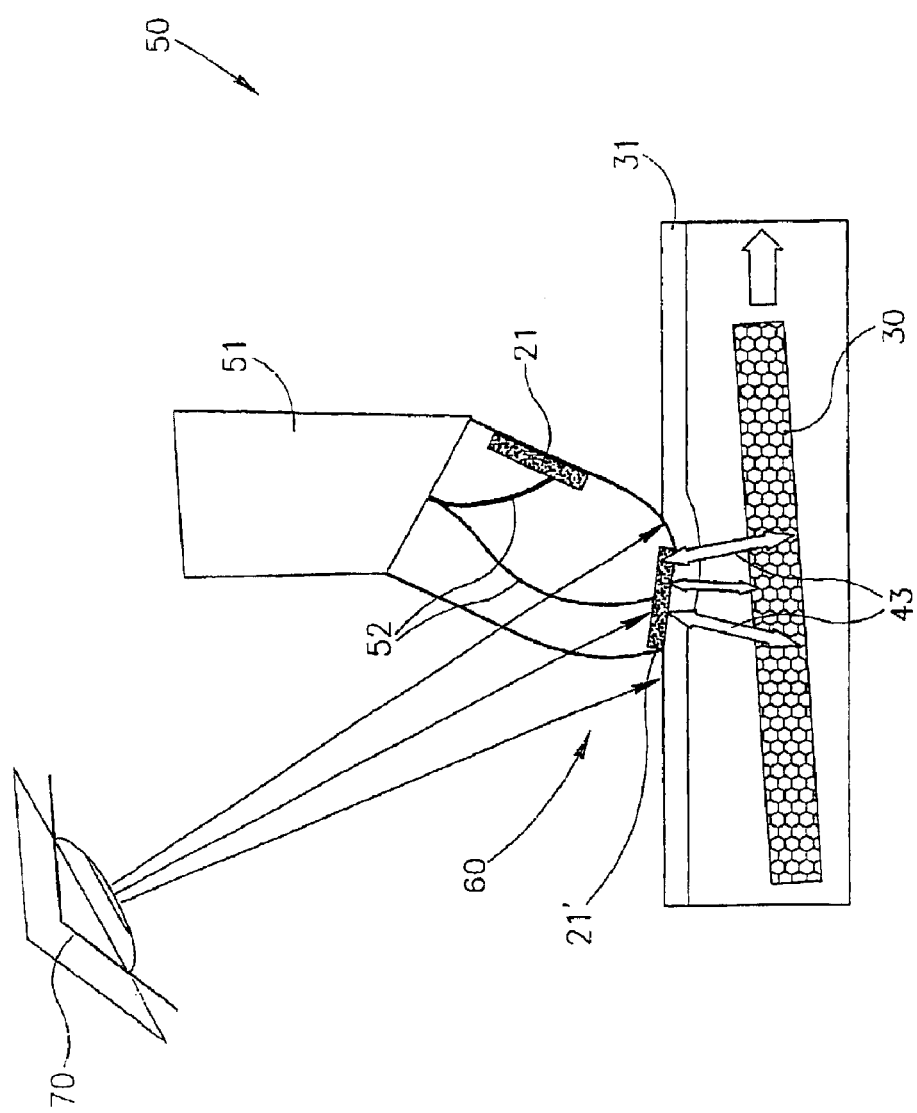
FIGS. 14A–14C are illustrations of the operation of apparatus of FIG. 12 according to several embodiments of the present invention.
Figure 14B:
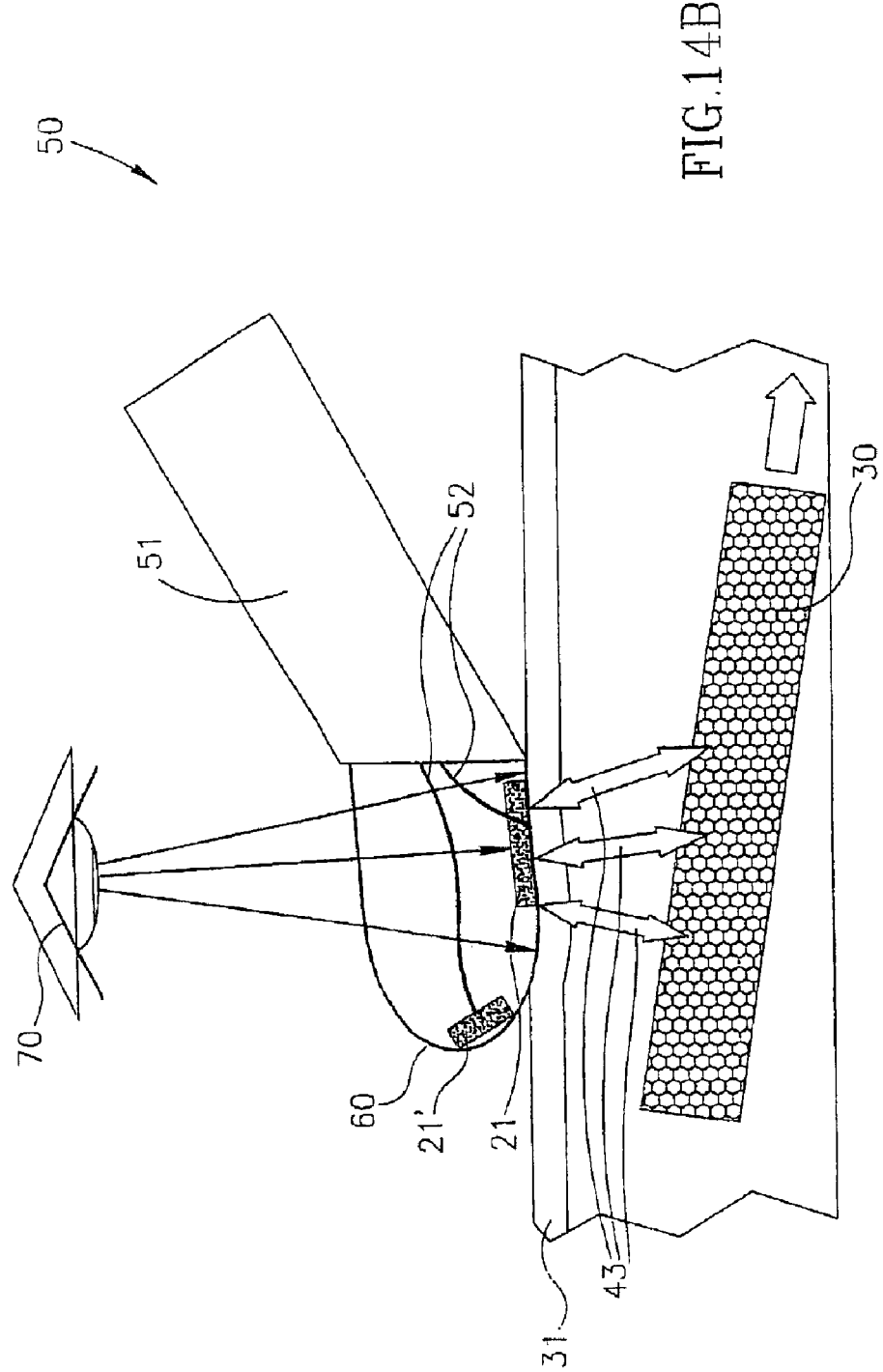
Figure 14C:
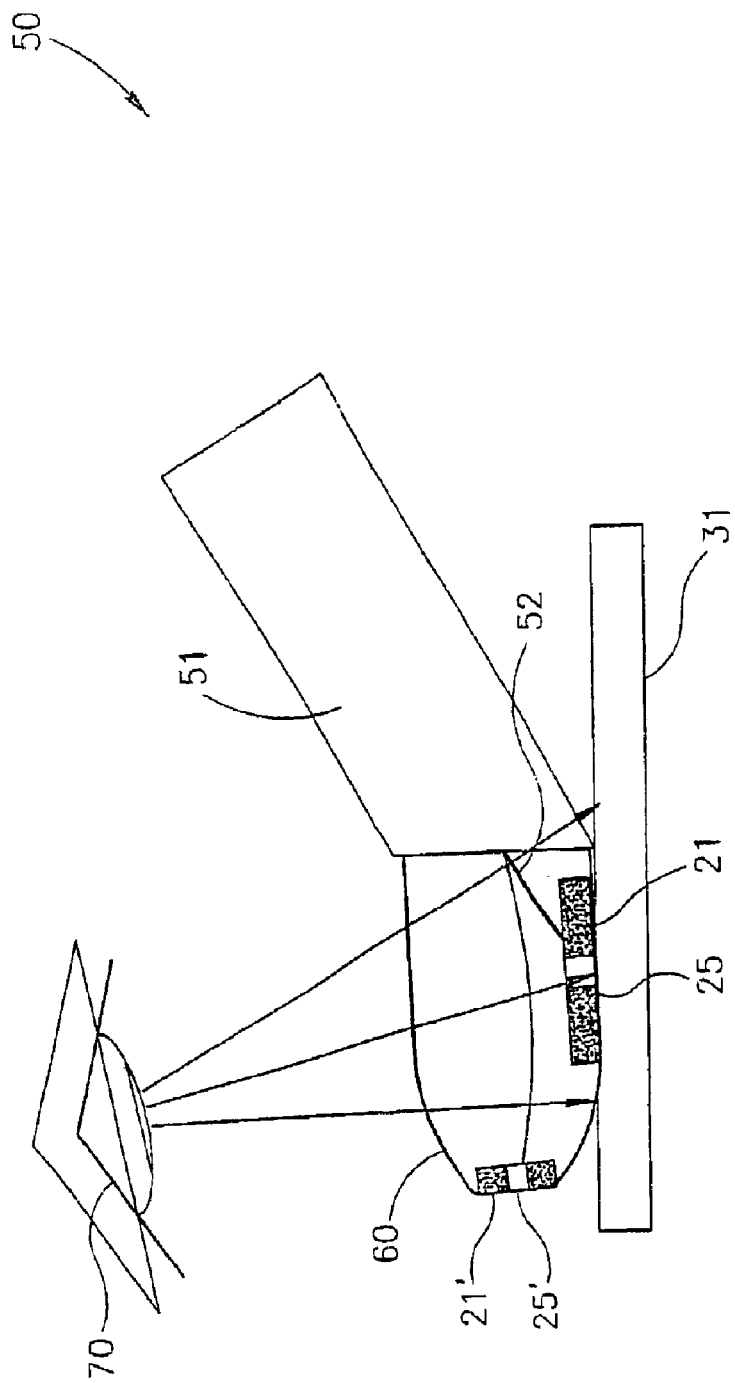

Reference is now made to FIGS. 14A–14C, which are side and bottom view illustrations of apparatus 50 in use, according to one embodiment of the present invention wherein apparatus 50 includes two transceivers 22 and 22'. The presence of two transceivers allows for wave penetration into both shallow, small vascular elements and large, deep ones. As shown in FIG. 14A, transceiver 22' located on the tip of housing 60, is configured to transmit waves in a range of 1–10 MHz. In one embodiment, waves of 8 MHz are transmitted. This frequency allows for penetration into small, shallow blood vessels 30. As shown in FIG. 14B, transceiver 22, located on the bottom portion of housing 60, is configured to transmit waves 43 in a range 1–10 MHz. In one embodiment, waves of 5 MHz are transmitted. This frequency allows for penetration into large, deep blood vessels 30. According to this configuration, a user may choose to evaluate different types of blood vessels using one apparatus, by choosing to use a higher frequency scanning unit or a lower frequency scanning unit. FIG. 14C is an illustration of a bottom view of apparatus 50. As shown in the illustration, transmitter 23 and receiver 24 are semicircular in shape. However, it should be readily apparent that any shape suitable for vibrating, transmitting and receiving waves may be used. The area 61 between and around the transmitter and receiver is typically transparent, thereby possibly increasing the precision of the diagnosis of the area that is tested.

Figure 15A:
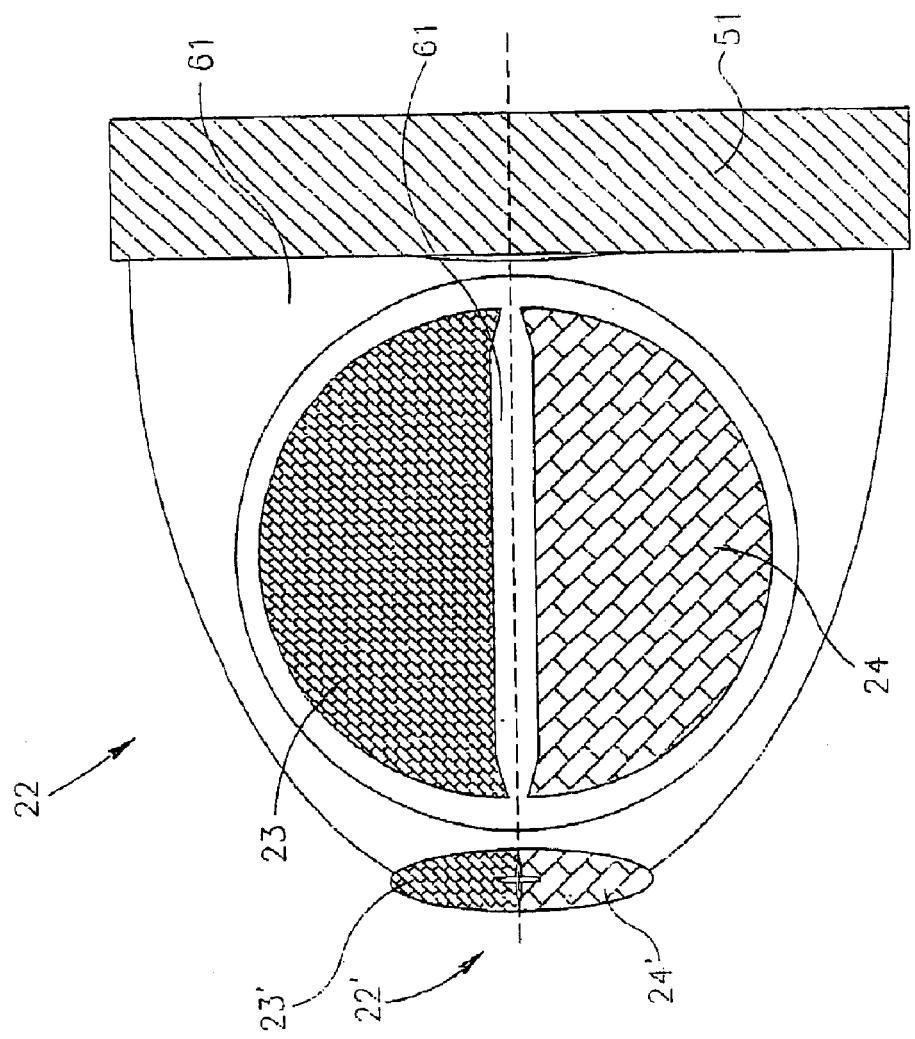
FIGS. 15A–15B are illustrations of the operation of apparatus of FIG. 12 according to other embodiments of the present invention.
Figure 15B:
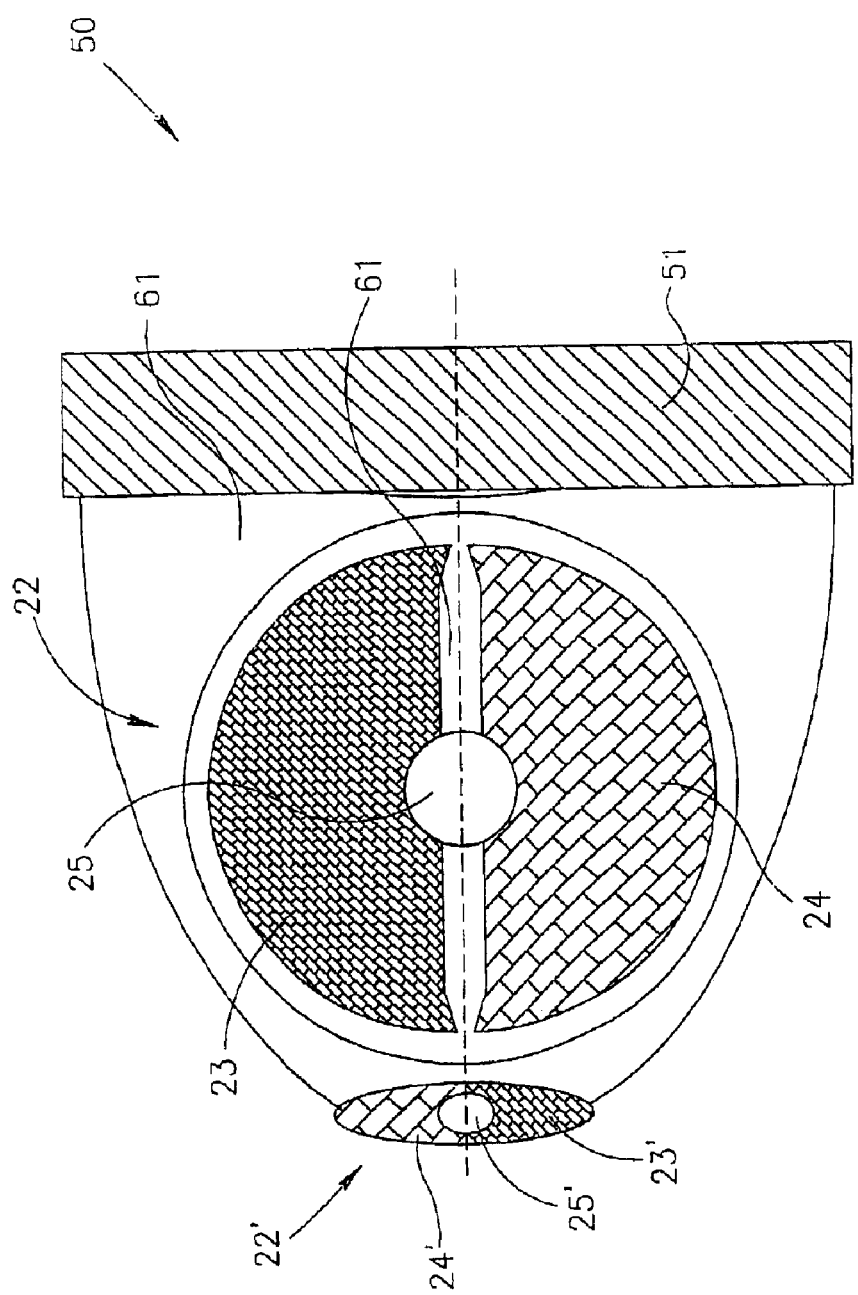

Reference is now made to FIGS. 15A–15B, which is an illustration of apparatus 50, according to one embodiment of the present invention in which two transceivers 21 and 21' of apparatus 50 have openings 25 and 25'. The openings 25 and 25' enable a view of specific marked spot on the skin as illustrated by eye 70 looking through the opening in transceiver 21, 21', 22 or 22'.

FIG. 15B is an illustration of a bottom view of apparatus 50. As shown in FIG. 15B, transmitter 23 and receiver 24 are semi-circular in shape and have a circular opening 25. The openings may be any suitable shape.

Figure 16B:
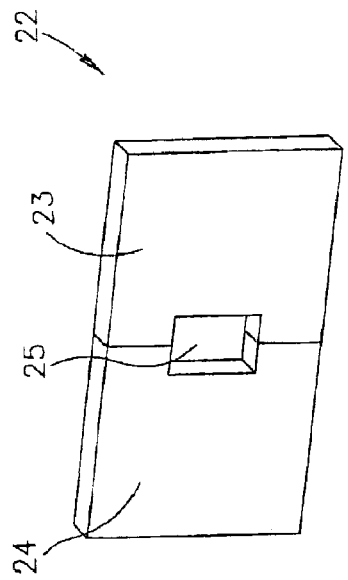
FIGS. 16A–16D are illustrations of various possible shapes of a transceiver according to some embodiments of the present invention.
Figure 16D:
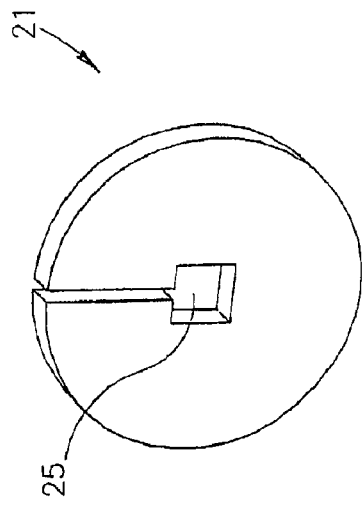
Figure 16A:
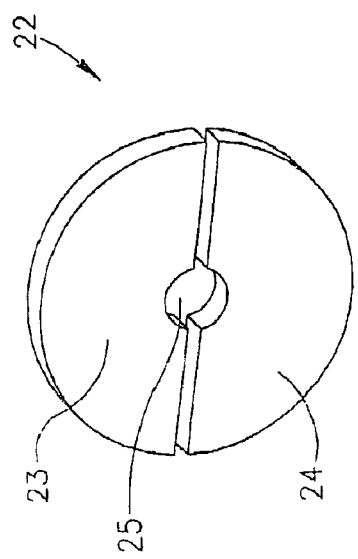
Figure 16C:
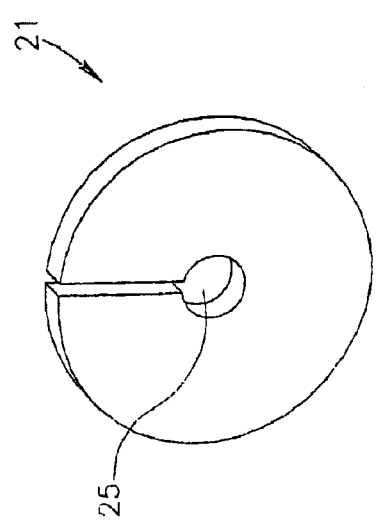

Reference is now made to FIGS. 16A–16D, which illustrate an embodiment of a piezo-ceramic transceiver 21 and 22 having openings. FIGS. 16A–16B illustrate two shapes of the two-block piezo-ceramic transceiver 22, having a circular and a rectangular opening 25. FIGS. 16C and 16D illustrate two shapes of the single-block piezo-ceramic transceiver 21, having a circular and a rectangular opening 25.

However, it should be readily apparent that multi block piezo-ceramic transceiver may be used. Furthermore, any shape suitable for vibrating, transmitting and receiving waves may be used. The area 61 between and around the transmitter and receiver may be transparent, as was shown in FIGS. 13, 14 and 15. Transmitters and receivers may be adapted to vibrate in the KHz and in the MHz frequency ranges. Thus, the scanning area and the sensitivity of device may be increased.

Figure 17B:
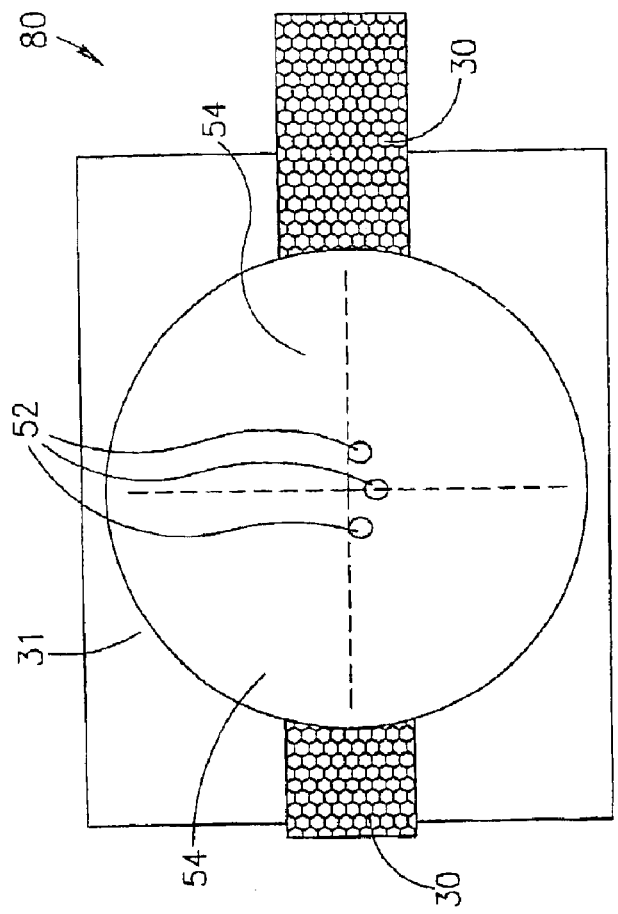
FIGS. 17A–17B are illustrations of an apparatus according to a further embodiment of the present invention.
Figure 17A:
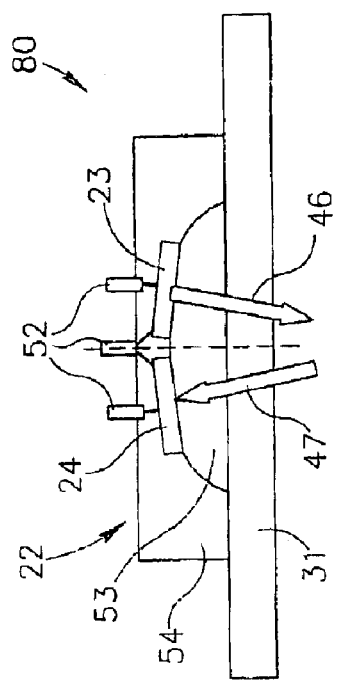

Reference is now made to FIGS. 17A and 17B, which are illustrations of a disposable sticker 80, according to another embodiment of the invention for vascular flow detection. As shown in FIG. 17A, a typically disposable sticker 80 includes a sticker 54 that includes two-block piezo-ceramic transceiver 22. Two-block piezo-ceramic transceiver 22, one block transceiver 21 or two-block transceiver 22 include transmitter 23 and receiver 24 on a acoustic matching layer 53, for example silicone pad, connected by wires 52 to a chip processor 10 including an audio or optical monitoring system. The disposable sticker 80 may be stuck to the skin 31 to enable the transmitting of waves 46 or receiving of waves 47 for the detection of blood flow.

FIG. 17B is a top view of apparatus 80 illustrating the sticker 54 over the blood vessel 30 and the connectors 52.

Disposable apparatus 80 may enable a fast and convenient detection of vascular flow in case of emergency. Also the apparatus may enable collection of information on vascular flow during movement of the patient and at one or at several spots. The information may be obtained using various conversion methods, for example comparing the received against the transmitted electrical waves. The information may include various parameters and other information regarding the blood vessel, such as rate of flow of blood through the vessel, etc. The information may be displayed to a user in audio and/or visual form according to any format known in the present or yet to be devised in the future.

Reference is now made to FIGS. 18A–18B, which are a side and top view illustrates the use of disposable sticker 80 for monitoring the vascular flow at three spots. The vascular flow output of each apparatus is transferred to a monitoring system 90 that includes a chip processor 10, by electric wires 52.

The system and apparatus described hereinabove is, of course, not limited to the use of blood flow monitoring but has many other applications where a lightweight, mechanically uncomplicated scanning system is required for miniature applications which is oscillating in its characteristic frequency. For example, the system can be used for monitoring hearth beats of a human or a fetus. The frequency of the piezoelement's vibrations depends on a number of factors which include geometrical parameters and shape as described herein, the number of electrodes on the piezoelement and the attachment points of the piezoelement to the fixed structure.

While some embodiments of the present invention have been described, so as to enable one of skill in the art to practice the present invention, the preceding description is intended to be exemplary only. It should not be used to limit the scope of the invention, which should be determined by reference to the following claims.

What is claimed is:

1. A method of detecting motion inside of a body, the method comprising:
providing an electrical signal to a piezoceramic transducer at a first frequency, to cause said transducer to transmit thickness vibrations to a target area;
providing an electrical signal to said piezoceramic transducer at a second frequency, said second frequency being a lower frequency than said first frequency, to cause said transducer to generate bending vibrations, thereby causing said thickness vibrations transmitted from said transducer to scan a relatively wide target area; and
receiving vibrations to said piezoceramic transducer, said vibrations resulting from said thickness vibrations being reflected from an element inside said wide target area.

2. The method of claim 1, further comprising calculating a velocity of a structure inside said wide target area by using a Doppler effect based on the reflected vibrations.

3. The method of claim 1, further comprising altering the pattern electrical signals provided to said transducer.

4. The method of claim 3, further comprising altering the pattern of vibrations emitted by said transducer.

5. The method according to claim 1, wherein said first frequency is in the MHZ range and said second frequency is in the KHZ range.

6. The method of claim 1, wherein said signal is selected from the group consisting of a burst wave input, a continuous wave input, and a standing wave input.

7. The method of claim 1 comprising configuring said at least one piezoceramic transducer to achieve variability in scanning.

8. The method of claim 1, comprising scanning said target area in the x, y, and z axes.

9. The method of claim 1, wherein said transducer enables mechanical scanning of said target at a wide range of angular orientations.

10. The method according to claim 1, comprising generating bending vibration waves that cause planar vibrations within said transceiver, thereby providing an angle suitable for receiving reflected vibrations from said relatively wide target area.

11. The method according to claim 1, comprising generating vibrations using a multi-block piezo-ceramic transceiver unit.

12. A motion detecting apparatus for detecting motion inside of a body, said apparatus comprising:
a piezoceramic transducer;
a first oscillator to provide an electrical signal to said piezoceramic transducer at a first frequency, to generate thickness vibrations for transmission to a target area;
a second oscillator to provide an electrical signal to said piezoceramic transducer at a second frequency, said second frequency being at a lower frequency than said first frequency, said signal being capable to cause said transducer to generate bending vibrations, thereby scanning a relatively wide target area; and
wherein said piezoceramic transducer is to receive vibrations reflected from said relatively wide target area, and to convert the reflected vibrations into electrical signals.

13. The motion detector according to claim 12, further comprising a signal detector to detect the electrical signals produced by said transducer.

14. The motion detector according to claim 12, further comprising a switching gate to switch the signal applied to said transducer between higher frequency signals and said lower frequency signals.

15. The motion detector according to claim 12, wherein said piezo-ceramic transducer has an opening.

16. The motion detector according to claim 12, wherein said transducer includes at least one transmitting element and at least one receiving element, said transmitting element(s) and said receiving element(s) being enabled to scan said relatively wide target area.

17. The motion detector according to claim 16, wherein electrical signals from said first and second oscillators are applied to all said transmitting elements and said receiving elements.

18. The motion detector according to claim 12, wherein said first oscillator produces an electric signal in the Megahertz range and said second oscillator produces an electric signal in the Kilohertz range.

19. The apparatus according to claim 12, further comprising a housing which is at least partially clear for said transducer.

20. The apparatus of claim 12 wherein said first oscillator is configured to provide an input selected from the group consisting of burst wave input, continuous wave input and standing vibration wave input.

21. The apparatus of claim 12, wherein said at least one piezoceramic transducer is configured to achieve variability in scanning.

22. The apparatus of claim 12, comprising a first piezo-ceramic transceiver unit and a second piezo-ceramic transceiver unit, wherein said first transducer is to provide a transmitting frequency of 5 MHz and said second transducer is to provide a transmitting frequency of 8 MHz.

23. The apparatus of claim 12, wherein said transducer scans a target using a wide angular range.

24. The apparatus of claim 23, wherein said angular range is determined by one or more of operations selected from the group consisting of attaching said transducer in one or more selected ways, the voltage applied to said transducer, and the frequency of signals applied to said transducer.

25. The apparatus according to claim 12, wherein said detecting apparatus is included within a chip.

* * * * *